(12) United States Patent
Kendall et al.

(10) Patent No.: US 9,283,365 B2
(45) Date of Patent: Mar. 15, 2016

(54) PATCH PRODUCTION

(71) Applicant: The University of Queensland, Queensland (AU)

(72) Inventors: Mark Anthony Fernance Kendall, Chelmer (AU); Derek William Kenneth Jenkins, Wantage (GB)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 14/508,451

(22) Filed: Oct. 7, 2014

(65) Prior Publication Data
US 2015/0224294 A1    Aug. 13, 2015

Related U.S. Application Data

(63) Continuation of application No. 12/866,717, filed as application No. PCT/AU2009/000142 on Feb. 5, 2009, now Pat. No. 8,883,015.

(60) Provisional application No. 61/063,932, filed on Feb. 7, 2008.

(51) Int. Cl.
*A61M 37/00* (2006.01)
*B81C 1/00* (2006.01)

(52) U.S. Cl.
CPC ........ *A61M 37/0015* (2013.01); *B81C 1/00111* (2013.01); *A61M 2037/0023* (2013.01); *A61M 2037/0046* (2013.01); *A61M 2037/0053* (2013.01); *B81B 2201/055* (2013.01)

(58) Field of Classification Search
CPC .. H01J 9/025; G01P 15/0802; B81C 1/00111; A61M 37/0015
USPC ........................................................ 216/2, 11
See application file for complete search history.

(56) References Cited

U.S. PATENT DOCUMENTS

| | | |
|---|---|---|
| 2,881,500 A | 4/1959 | Furness |
| 4,702,799 A | 10/1987 | Tuot |
| 5,201,992 A | 4/1993 | Marcus et al. |
| 5,353,792 A | 10/1994 | Lübbers et al. |
| 5,449,064 A | 9/1995 | Hogan et al. |
| 5,457,041 A | 10/1995 | Ginaven et al. |
| 5,499,474 A | 3/1996 | Knooihuizen |

(Continued)

FOREIGN PATENT DOCUMENTS

| | | |
|---|---|---|
| CN | 101014395 A | 7/2008 |
| CN | 101297989 A | 11/2008 |

(Continued)

OTHER PUBLICATIONS

International Preliminary Report on Patentability, mailed Jul. 8, 2010, for International Application No. PCT/AU2008/001903, 8 pages.

(Continued)

*Primary Examiner* — Stewart Fraser
(74) *Attorney, Agent, or Firm* — Seed IP Law Group PLLC

(57) ABSTRACT

A method of producing projections on a patch including providing a mask on a substrate and etching the substrate using an etchant and a passivant to thereby control the etching process and form the projections, wherein the passivant does not include oxygen.

27 Claims, 25 Drawing Sheets

(56) References Cited

U.S. PATENT DOCUMENTS

| | | | |
|---|---|---|---|
| 5,527,288 | A | 6/1996 | Gross et al. |
| 5,611,806 | A | 3/1997 | Jang |
| 5,859,937 | A | 1/1999 | Nomura |
| 5,922,356 | A | 7/1999 | Koseki et al. |
| 5,928,207 | A | 7/1999 | Pisano et al. |
| 6,052,652 | A | 4/2000 | Lee |
| 6,287,556 | B1 | 9/2001 | Portnoy et al. |
| 6,299,621 | B1 | 10/2001 | Fogarty et al. |
| 6,334,856 | B1 | 1/2002 | Allen et al. |
| 6,352,697 | B1 | 3/2002 | Cox et al. |
| 6,454,755 | B1 | 9/2002 | Godshall |
| 6,463,312 | B1 | 10/2002 | Bergveld et al. |
| 6,478,738 | B1 | 11/2002 | Hirabayashi et al. |
| 6,503,231 | B1 | 1/2003 | Prausnitz et al. |
| 6,551,849 | B1 | 4/2003 | Kenney |
| 6,557,849 | B2 | 5/2003 | Wyss |
| 6,558,361 | B1 | 5/2003 | Yeshurun |
| 6,589,202 | B1 | 7/2003 | Powell |
| 6,591,124 | B2 | 7/2003 | Sherman et al. |
| 6,743,211 | B1 | 6/2004 | Prausnitz et al. |
| 6,749,575 | B2 | 6/2004 | Matriano et al. |
| 6,855,372 | B2 | 2/2005 | Trautman et al. |
| 6,908,453 | B2 | 6/2005 | Fleming et al. |
| 6,923,764 | B2 | 8/2005 | Aceti et al. |
| 6,931,277 | B1 | 8/2005 | Yuzhakov et al. |
| 6,945,952 | B2 | 9/2005 | Kwon |
| 7,022,071 | B2 | 4/2006 | Schaupp et al. |
| 7,045,069 | B2 | 5/2006 | Ozeryansky |
| 7,097,631 | B2 | 8/2006 | Trautman et al. |
| 7,169,600 | B2 | 1/2007 | Hoss et al. |
| 7,211,062 | B2 | 5/2007 | Kwon |
| 7,250,037 | B2 | 7/2007 | Shermer et al. |
| 7,753,888 | B2 | 7/2010 | Mukerjee et al. |
| 8,052,633 | B2 | 11/2011 | Kendall |
| 8,062,573 | B2 | 11/2011 | Kwon |
| 8,734,697 | B2 | 5/2014 | Chen et al. |
| 8,883,015 | B2 | 11/2014 | Kendall et al. |
| 2002/0008530 | A1* | 1/2002 | Kim et al. .................... 324/754 |
| 2002/0016562 | A1 | 2/2002 | Cormier et al. |
| 2002/0128599 | A1 | 9/2002 | Cormier et al. |
| 2002/0177839 | A1 | 11/2002 | Cormier et al. |
| 2003/0036710 | A1 | 2/2003 | Matriano et al. |
| 2003/0199810 | A1 | 10/2003 | Trautman et al. |
| 2004/0002121 | A1 | 1/2004 | Regan et al. |
| 2004/0039397 | A1 | 2/2004 | Weber et al. |
| 2005/0042866 | A1 | 2/2005 | Klapproth et al. |
| 2005/0126710 | A1* | 6/2005 | Laermer et al. .......... 156/345.33 |
| 2005/0137531 | A1 | 6/2005 | Prausnitz et al. |
| 2005/0143713 | A1 | 6/2005 | Delmore et al. |
| 2005/0197308 | A1 | 9/2005 | Dalton et al. |
| 2005/0261632 | A1 | 11/2005 | Xu |
| 2006/0015061 | A1 | 1/2006 | Kuo et al. |
| 2006/0055724 | A1* | 3/2006 | Krawczyk et al. ............... 347/20 |
| 2006/0074376 | A1 | 4/2006 | Kwon |
| 2006/0195125 | A1 | 8/2006 | Sakakine et al. |
| 2006/0264782 | A1 | 11/2006 | Holmes et al. |
| 2007/0027474 | A1 | 2/2007 | Lasner |
| 2007/0060867 | A1 | 3/2007 | Xu |
| 2007/0078376 | A1 | 4/2007 | Smith |
| 2007/0224252 | A1 | 9/2007 | Trautman et al. |
| 2007/0264749 | A1 | 11/2007 | Birkmeyer |
| 2007/0270738 | A1 | 11/2007 | Wu |
| 2007/0299388 | A1 | 12/2007 | Chan et al. |
| 2008/0108959 | A1 | 5/2008 | Jung et al. |
| 2008/0245764 | A1* | 10/2008 | Pirk et al. .......................... 216/2 |
| 2008/0312669 | A1 | 12/2008 | Vries et al. |
| 2010/0221314 | A1 | 9/2010 | Matsudo et al. |
| 2010/0222743 | A1 | 9/2010 | Frederickson et al. |
| 2011/0028905 | A1 | 2/2011 | Takada |
| 2011/0059150 | A1 | 3/2011 | Kendall et al. |
| 2011/0160069 | A1 | 6/2011 | Corrie et al. |
| 2011/0223542 | A1 | 9/2011 | Kendall |
| 2011/0245776 | A1 | 10/2011 | Kendall |
| 2011/0288484 | A1 | 11/2011 | Kendall et al. |
| 2012/0027810 | A1 | 2/2012 | Chen et al. |
| 2012/0083741 | A1 | 4/2012 | Kendall |
| 2012/0083762 | A1 | 4/2012 | Kendall |
| 2012/0330250 | A1 | 12/2012 | Kuwahara et al. |
| 2013/0190794 | A1 | 7/2013 | Kendall et al. |
| 2014/0257188 | A1 | 9/2014 | Kendall et al. |

FOREIGN PATENT DOCUMENTS

| | | |
|---|---|---|
| EP | 0 139 286 A2 | 5/1985 |
| EP | 1 695 734 B1 | 6/2008 |
| EP | 2 327 419 A1 | 6/2011 |
| JP | 2007-260889 A | 10/2007 |
| WO | 91/06571 A1 | 5/1991 |
| WO | 94/24281 A1 | 10/1994 |
| WO | 98/28037 A1 | 7/1998 |
| WO | 99/02694 A1 | 1/1999 |
| WO | 99/42564 A2 | 8/1999 |
| WO | 99/06480 A1 | 12/1999 |
| WO | 00/05339 A1 | 2/2000 |
| WO | 00/42215 A1 | 7/2000 |
| WO | 00/74763 A3 | 12/2000 |
| WO | 00/74764 A1 | 12/2000 |
| WO | 01/33614 A2 | 5/2001 |
| WO | 02/064193 A2 | 8/2002 |
| WO | 02/074173 A1 | 9/2002 |
| WO | 02/075794 A1 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | 2005/060621 A1 | 7/2005 |
| WO | 2005/069736 A2 | 8/2005 |
| WO | 2005/072630 A1 | 8/2005 |
| WO | 2005/123173 A1 | 12/2005 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A2 | 12/2006 |
| WO | 2007/002123 A2 | 1/2007 |
| WO | 2007/002521 A2 | 1/2007 |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/070004 A1 | 6/2007 |
| WO | 2007/080427 A2 | 7/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2009/040548 A1 | 4/2009 |
| WO | 2009/066763 A1 | 5/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 01/85207 A2 | 11/2011 |

OTHER PUBLICATIONS

International Preliminary Report on Patentability, completed Nov. 14, 2012, for International Application No. PCT/AU2011/000890, 6 pages.

(56) References Cited

OTHER PUBLICATIONS

International Preliminary Report on Patentability, mailed Jun. 7, 2006, for International Application No. PCT/GB2005/000336, 11 pages.
International Search Report, mailed Feb. 20, 2009, for International Application No. PCT/AU2008/001903, 5 pages.
International Search Report, mailed Oct. 25, 2011, for International Application No. PCT/AU2011/000890, 4 pages.
International Search Report, mailed Feb. 20, 2013, for International Application No. PCT/AU2012/001289, 13 pages.
Widera et al., "Effect of delivery parameters on immunization to ovalbumin following intracutaneous administration by a coated microneedle array patch system," *Vaccine* 24:1653-1664, 2006.
Written Opinion of the International Searching Authority, mailed Feb. 20, 2009, for International Application No. PCT/AU2008/001903, 6 pages.
Aichele et al., "Antiviral Cytotoxic T Cell Response Induced by In Vivo Priming With a Free Synthetic Peptide," *Journal of Experimental Medicine* 171:1815-1820, May 1990.
Albert et al., "Dendritic cells acquire antigen from apoptotic cells and induce class I-restricted CTLs," *Nature* 392(6671):86-89, Mar. 1998.
Albert et al., "Tumor-specific killer cells in paraneoplastic cerebellar degeneration," *Nature Medicine* 4 (11):1321-1324, Nov. 1998.
Anderson, "Cutaneous Microdialysis: Is it Worth the Sweat?," *Journal of Investigative Dermatology* 126:1207-1209, 2006.
Athanasopoulos et al., "Gene therapy vectors based on adeno-associated virus: characteristics and applications to acquired and inherited diseases (Review)," *International Journal of Molecular Medicine* 6(4):363-375, 2000.
Bachmann et al., "Dendritic cells process exogenous viral proteins and virus-like particles for class I presentation to CD8+ cytotoxic T lymphocytes," *European Journal of Immunology* 26(11):2595-2600, 1996.
Camilli et al., "*Listeria monocytogenes* Mutants Lacking Phosphatidylinositol-specific Phospholipase C Are Avirulent," *Journal of Experimental Medicine* 173:751-754, Mar. 1991.
Cormier et al., "Transdermal delivery of desmopressin using a coated microneedle array patch system," *Journal of Controlled Release* 97(3):503-511, 2004.
Cox et al., "Adjuvants—a classification and review of their modes of action," *Vaccine* 15(3):248- 256, 1997.
Dreyer, "Microneedles: Microprocessing in medicine," Final Presentation, ENMA465 Project, URL= http://www.mse.umd.edu/undergrad/courses/ENMA465-project-results.html, May 10, 2004, 23 pages.
Feng et al., "Molecular Biomarkers for Cancer Detection in Blood and Bodily Fluids," *Critical Reviews in Clinical Laboratory Sciences* 43(5-6):497-560, 2006.
Gao et al., "Priming of influenza virus-specific cytotoxic T lymphocytes vivo by short synthetic peptides," *Journal of Immunology* 147(10):3268-3273, Nov. 1991.
Gardeniers et al., "Silicon Micromachined Hallow Microneedles for Transdermal Liquid Transport," *Journal of Microelectromechanical Systems* 12(6):855-862, 2003.
Gill et al., "Coated microneedles for transdermal delivery," *Journal of Controlled Release* 117(2):227-237, 2007.
Gill et al., "Coating formulations for Microneedles," *Pharmaceutical Research* 24(7):1369-1380, Jul. 2007.
Ito et al., "Evaluation of self-dissolving needles containing low molecular weight heparin (LMWH) in rats," *International Journal of Pharmaceutics* 349(1-2):124-129, 2008.
Ito et al., "Feasibility of microneedles for percutaneous absorption of insulin," *European Journal of Pharmaceutical Sciences* 29(1):82-88, 2006.
Ito et al., "Self-dissolving microneedles for the percutaneous absorption of EPO in mice," *Journal of Drug Targeting* 14(5):255-261, 2006.
Jondal et al., "MHC Class I—Restricted CTL Responses to Exogenous Antigens," *Immunity* 5(4):295-302, Oct. 1996.
Lin et al., "Silicon-Processed Microneedles," *IEEE Journal of Microelectromechanical Systems* 8(1):78-84, 1999.
Kay et al., "Viral vectors for gene therapy: the art of turning infectious agents into vehicles of therapeutics," *Nature Medicine* 7(1):33-40, Jan. 2001.
Kendall et al., "The mechanical properties of the skin epidermis in relation to targeted gene and drug delivery," *Biomaterials* 28(33): 4968-4977, 2007.
Kuzu et al., "In vivo priming effect during various stages of ontogeny of an influenza A virus nucleoprotein peptide," *European Journal of Immunology* 23(6):1397-1400, 1993.
Kwon, "Acne Treatment by a Dissolvable Micro-Needle Patch," Controlled Release Society 33rd Annual Meeting, 2006, 2 pages.
Kwon, "In Vitro Evaluation of Transdermal Drug Delivery by a Micro-needle Patch," Abstract #115, Controlled Release Society 31st Annual Meeting Transactions, 2004, 2 pages.
Kwon, "In Vitro Modeling of Transdermal PTH Delivery by Dissolving Micro-needle Patch," TheraJect Web Site (2007), 2 pages.
Kwon, "Rapid Intradermal Drug Delivery by a Dissolvable Micro-Needle Patch," Abstract #306, Controlled Release Society 32nd Annual Meeting & Exposition Transactions, 2005, 2 pages.
Lee et al., "Dissolving microneedles for transdermal drug delivery," *Biomaterials* 29(13):2113-2124, 2008.
Matriano et al., "Macroflux® Microprojection Array Patch Technology: A New and Efficient Approach for Intracutaneous Immunization," *Pharmaceutical Research* 19(1):63-70, Jan. 2002.
Mengaud et al., "Expression in *Escherichia coli* and Sequence Analysis of the Listeriolysin O Determinant of *Listeria monocytogenes*," *Infection and Immunity* 56(4):766-772, Apr. 1988.
Miyano et al., "Hydrolytic Microneedles as Transdermal Drug Delivery System," *International Solid-State Sensors, Actuators and Microsystems Conference Transducers 2007*, pp. 355-358, Jun. 10-14, 2007.
Miyano et al., "Sugar Micro Needles as Transdermic Drug Delivery System," *Biomedical Microdevices* 7(3):185-188, 2005.
Moore et al., "Introduction of soluble protein into the class I pathway of antigen processing and presentation," *Cell* 54(6):777-785, Sep. 9, 1988.
Mukerjee et al., "Microneedle array for transdermal biological fluid extraction and in situ analysis," *Sensors and Actuators A* 114:267-275, 2004.
Office Action, mailed Feb. 17, 2012, for Chinese Application No. 200980104635.3, 7 pages. (with English Translation).
Oh et al., "Demonstration of Dose-controlled Delivery by Dissolvable Micro-needle Arrays," Controlled Release Society 34th Annual Meeting and Exposition Jun./Jul. 7-11, 2007, 2 pages.
Oh et al., "Intradermal influenza vaccine delivery using skin-penetrating dissolvable vaccine microneedles," AAPS Annual Meeting and Exposition, 2006, 1 page.
Palmer et al., "Streptolysin O: a proposed model of allosteric interaction between a pore-forming protein and its target lipid bilayer," *Biochemistry* 37(8):2378-2383, Feb. 1998.
Park et al., "Biodegradable polymer microneedles: Fabrication, mechanics and transdermal drug delivery," *Journal of Controlled Release* 104:51-66, 2005.
Park et al., "Polymer Microneedles for Controlled-Release Drug Delivery," *Pharmaceutical Research* 23(5):1008-1019, May 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O to Mediate growth of *Bacillus subtilis* within Mammalian Cells," *Infection and Immunity* 60(7):2710-2717, Jul. 1992.
Rossjohn et al., "Structure of a Cholesterol-Binding, Thiol-Activated Cytolysin and a Model of Its Membrane Form," *Cell* 89(5):685-692, May 30, 1997.
Schulz et al., "Peptide-induced antiviral protection by cytotoxic T cells," *Proceedings of the National Academy of Sciences USA* 88:991-993, Feb. 1991.
Silver et al., "Viscoelastic properties of young and old human dermis: A proposed molecular mechanism for elastic energy storage in collagen and elastin," *Journal of Applied Polymer Science* 86(8):1978-1985, Nov. 2002.

(56) References Cited

OTHER PUBLICATIONS

Stoeber et al., "Arrays of Hallow Out-of-Plane Microneedles for Drug Delivery," *Journal of Microelectromechanical Systems 14*(3):472-479, 2005.
Sullivan et al., "Minimally Invasive Protein Delivery with Rapidly Dissolving Polymer Microneedles," *Adv.Mater.20*(5):933-938, Mar. 2008.
Tao et al., "A systematic study of dry etch process for profile control of silicon tips," *Microelectronic Engineering 78-79*:147-151, 2005.
Tsuchiya et al., "Development of Blood Extraction System for Health Monitoring System," *Biomedical Microdevices 7*(4):347-353, 2005.
Tyagi et al., "Molecular Beacons: Probes that Fluoresce upon Hybridization," *Nature Biotechnology 14*(3):303-308, 1996.
Vigna et al., "Lentiviral vectors: excellent tools for experimental gene transfer and promising candidates for gene therapy," *Journal of Gene Medicine 2*(5):308-316, Sep./Oct. 2000.
Walther et al., "Viral Vectors for Gene Transfer: A Review of Their Use in the Treatment of Human Diseases," *Drugs 60*(2):249-271, Aug. 2000.
Wang et al., "Label-free hybridization detection of a single nucleotide mismatch by immobilization of molecular beacons on an agarose film," Nucleic Acids Research 30(12):e61, 2002, 9 pages.
Wu et al., "Production of viral vectors for gene therapy applications," *Current Opinion in Biotechnology 11*(2):205-208, Apr. 2000.
Yuan et al., "Measuring microelastic properties of stratum corneum," *Colloids and Surfaces B: Biointerfaces 48*(1):6-12, Mar. 1, 2006.
Zheng et al., "Multiplexed electrical detection of cancer markers with nanowire sensor arrays," Nature Biotechnology 23(10):1294-1301, 2005.
Zhou et al., "Liposome-Mediated Cytoplasmic Delivery of Proteins: An Effective Means of Accessing the MHC Class I-Restricted Antigen Presentation Pathway," *Immunomethods 4*(3):229-235, 1994.
Crichton et al., "The viscoelastic, hyperelastic and scale dependent behavior of freshly excised individual skin layers," *Biomaterials 32*:4670-4681, 2011.
Fernando et al., "Potent Immunity to Low Doses of Influenza Vaccine by Probabilistic Guided Micro-Targeted Skin Delivery in a Mouse Model," *PLoS One 5*(4):e10266, 2010, 11 pages.
Henry et al., "Microfabricated Microneedles: A Novel Approach to Transdermal Drug Delivery," *Journal of Pharmaceutical Sciences 87*(8):922-925, Aug. 1998.
McAllister et al., "Microfabricated needles for transdermal delivery of macromolecules and nanoparticles: Fabrication methods and transport studies," *PNAS 100*(24):13755-13760, Nov. 25, 2003.

* cited by examiner

Fig. 23A
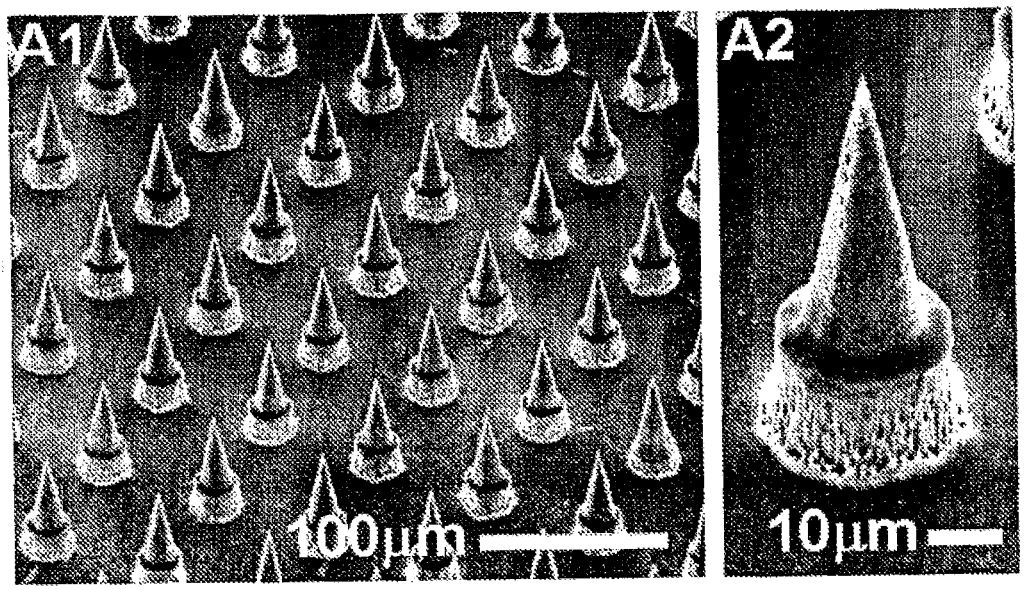
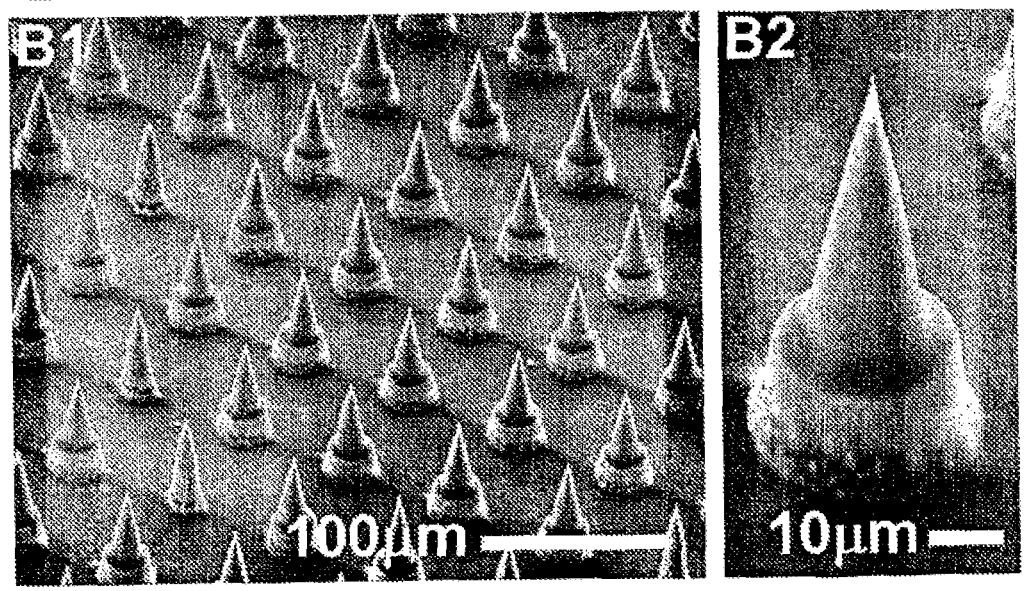
Fig. 23B

Fig. 24A
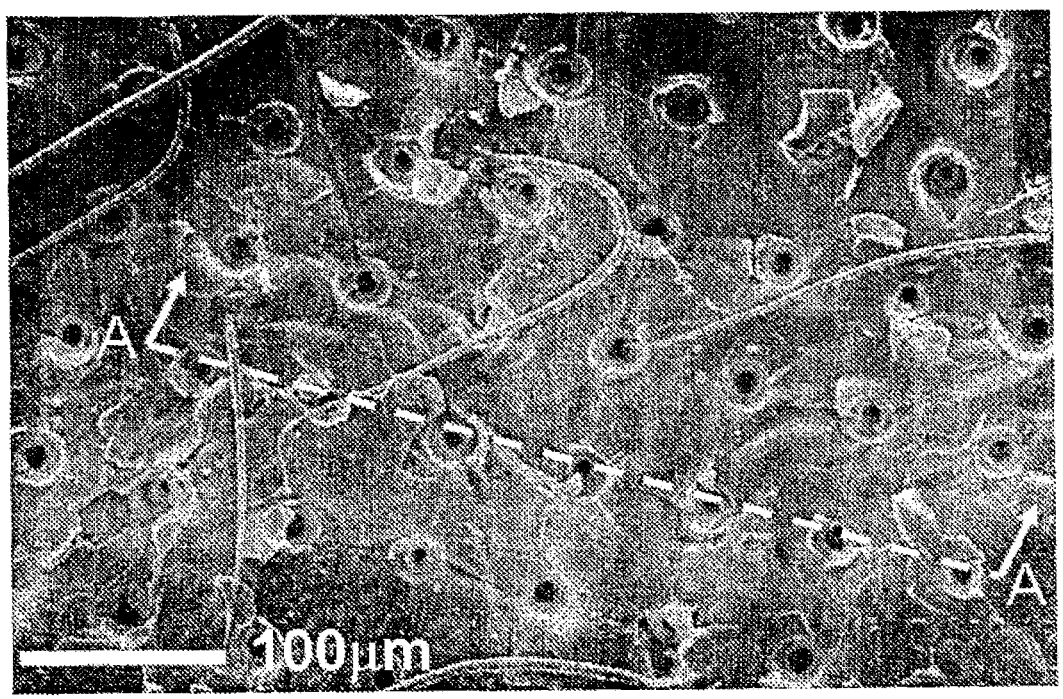
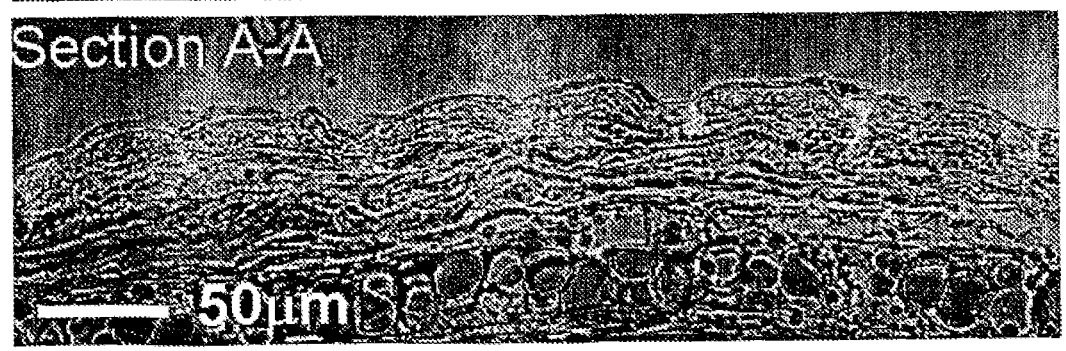
Fig. 24B

Fig. 25A
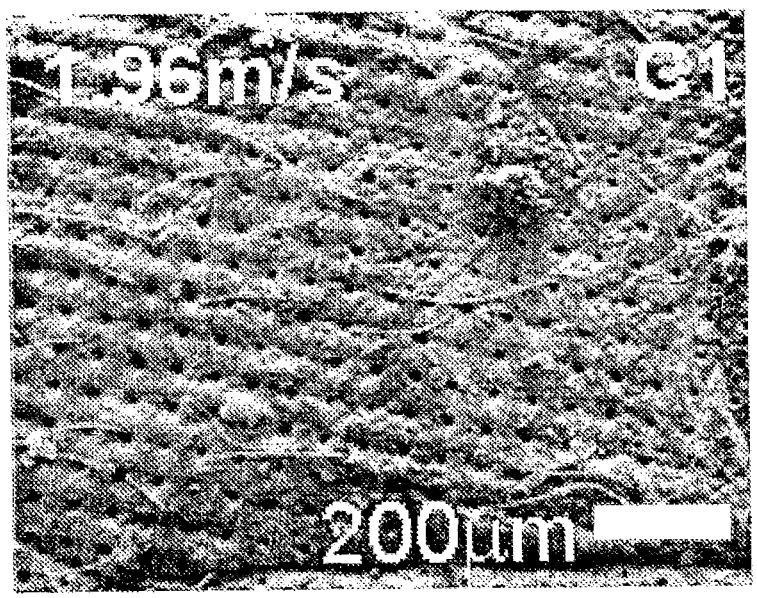
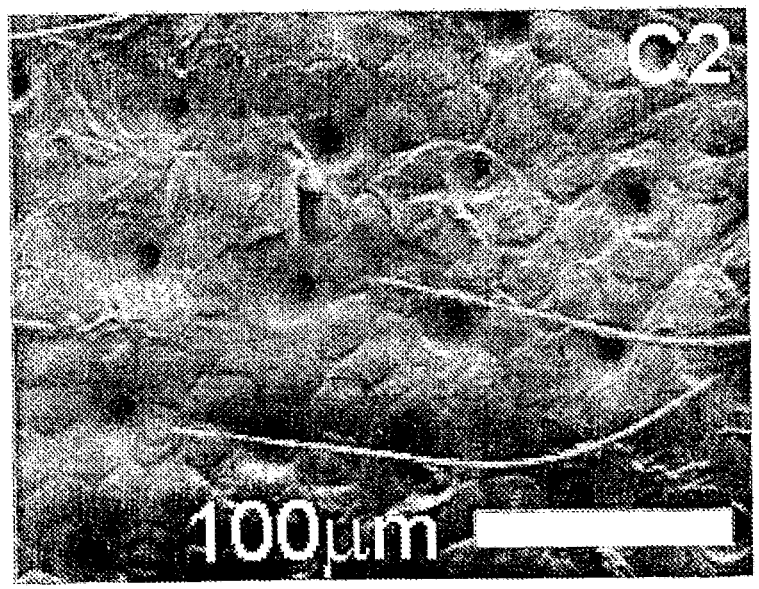
Fig. 25B

Fig. 26A
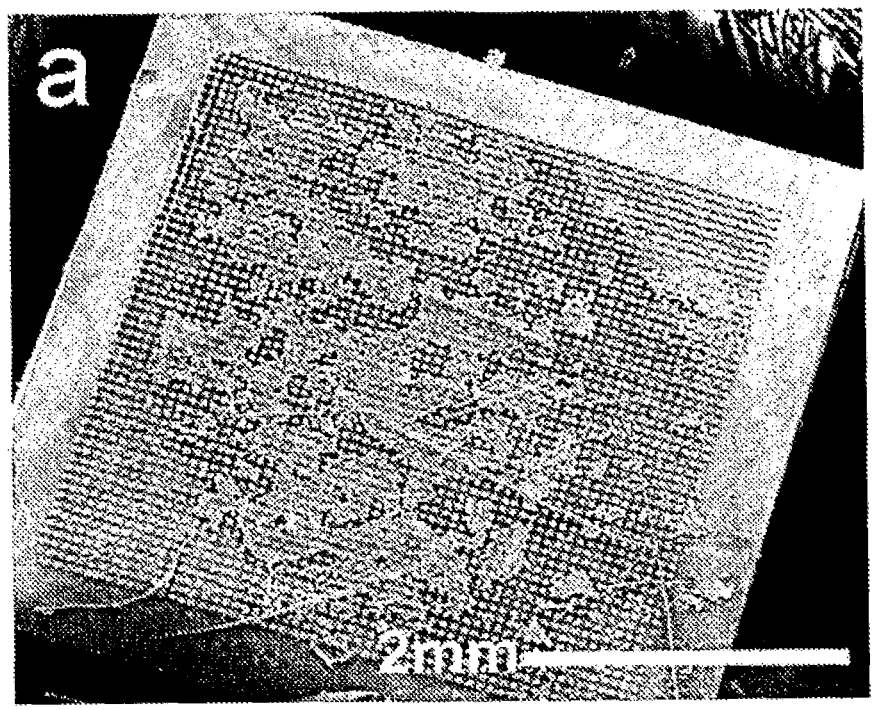
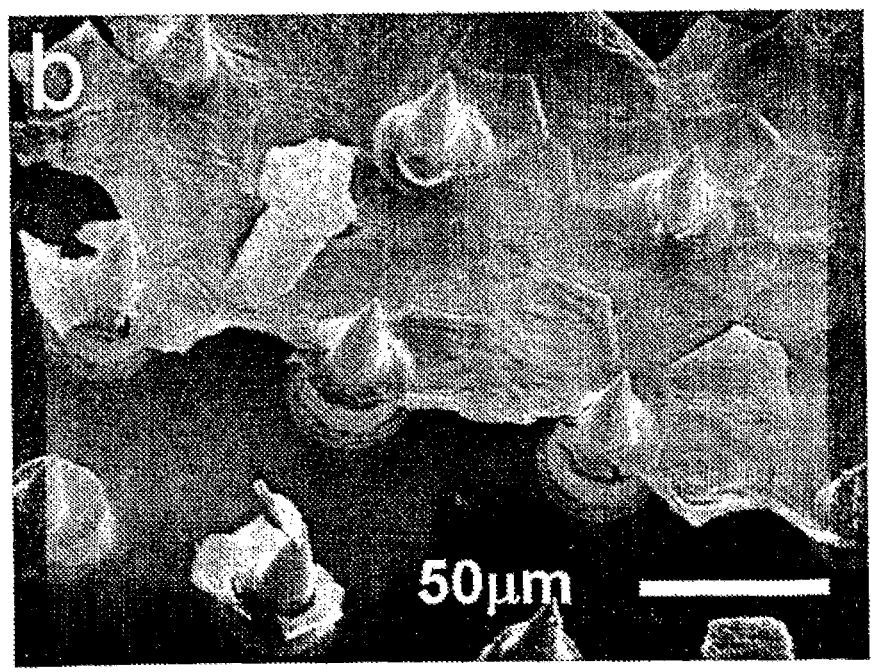
Fig. 26B

PATCH PRODUCTION

BACKGROUND OF THE INVENTION

The present invention relates to a method and apparatus for producing projections provided on a patch, and in particular to a method and apparatus for producing projections by etching a substrate.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to provide patches including a number of projections thereon to allow bioactive material or stimulus to be administered to a subject. Such arrays of projections or needles on a patch are an increasingly effective way of delivering stimulus, therapeutic agents or biomarkers since there is minimal or no pain, little or no injury from the syringe needle and highly reduced possibility of cross infection.

For example, WO2005/072630 describes devices for delivering bioactive materials and other stimuli to living cells, methods of manufacture of the device and various uses of the device, including a number of medical applications. The device comprises a plurality of projections which can penetrate a body surface so as to deliver the bioactive material or stimulus to the required site. The projections are typically solid and the delivery end section of the projection is so dimensioned as to be capable of insertion into targeted cells to deliver the bioactive material or stimulus without appreciable damage to the targeted cells or specific sites therein.

In order to function correctly, the projections typically need to have a sufficient length to pierce the stratum corneum. Examples of the projections include sub-millimeter and micron sized needles or blades that can be effective in delivering material through the skin.

A number of different techniques have been proposed for forming patches of needles.

For example, U.S. Pat. No. 6,334,856 and U.S. Pat. No. 6,503,231 describes microneedle devices for transport of therapeutic and biological molecules across tissue barriers. In this process, an appropriate masking material (e.g., metal) is deposited onto a silicon wafer substrate and patterned into dots. The wafer is then subjected to plasma based on fluorine/oxygen chemistries to etch very deep, high aspect ratio trenches into the silicon.

U.S. Pat. No. 5,201,992 describes methods for forming tapered silicon structures, of interest for use in atomic force microscopes, in field-emission devices, and in solid state devices are made using silicon processing technology. Resulting tapered structures have, at their tip, a radius of curvature of 10 manometers or less. Such preferred silicon structures are particularly suited as electron emitters in display devices.

However, the projections produced using fluorine/oxygen based etching tend to have a concave profile, particularly when applied to projections having a length of less than 500 µm, resulting in a narrow tip, which is thin and liable to breakage. This limits the ability of such projections to adequately deliver stimulus or material to a subject, which in turn limits their effectiveness.

Etching processes tend to lead to a bullseye effect, in which there are variations in the effectiveness of the etching process across a wafer being etched. As a result, when a wafer is divided into patches, some of the patches are unusable as they are inadequately or over etched. In fluorine/oxygen etching process, the bullseye effect tends to lead to a high percentage of unusable patches, such as about 40%. This high rate of inefficiency leads to high production costs due to the expense of the wafer material.

Additionally, these prior art techniques typically require a hard mask material such as metal mask, in order to allow the process to be performed. Such masks are difficult and expensive to obtain and use, thereby further hindering the production of useable patches using the prior art techniques.

U.S. Pat. No. 6,551,849 describes an alternative technique that involves forming an array of micro-needles by creating an array pattern on the upper surface of a silicon wafer and etching through openings in the pattern to define micro-needle sized cavities having a desired depth, to thereby form a mould. The mould thus formed may be filled with electrically conductive material, after which a desired fraction of the silicon wafer bulk is removed from the bottom-up by etching, to expose an array of projecting micro-needles.

However, all of the above described methods also require a significant number of processes to manufacture a micro-needle array. This tends to make the manufacturing process slow and difficult to reproduce with suitable quality, in high volume and in short time scales, which in turn leads to the production process being extremely expensive, particularly on a commercial scale.

As a result, recent developments in producing needle patches have focused on other manufacturing techniques, such as chemical vapour deposition, dopant diffusion, electron beam machining, wet and dry etching, laser cutting, masking, oxidation, photo-lithography, physical vapour deposition and scribing.

However, these other techniques are also proving ineffective at mass producing needle patches of suitable physical properties at an economic rate. As a result, the prior methods and devices for the delivery of material through the skin have exhibited limited success in transferring laboratory scale investigations to industrial scale production.

SUMMARY OF THE PRESENT INVENTION

The present invention seeks to ameliorate any one or more of the disadvantages of the prior art.

In a first broad form the present invention provides a method of producing projection on a patch, the method including:

a) providing a mask on a substrate; and, b) etching the substrate using an etchant and a passivant to thereby control the etching process and form the projections, wherein the passivant does not include oxygen.

Typically the mask includes an organic photo-resist.

Typically the passivant is a gas including:

a) at least one of:
   i) carbon; and,
   ii) silicon; and,
b) at least one of:
   i) chlorine; and,
   ii) fluorine.

Typically the passivant is at least one of:
a) a per-fluoride hydrocarbon; and,
b) a fluorinated olefine;
c) Octafluorocyclobutane;
d) Perfluoroisobutene; and,
e) $C_4F_8$.

Typically the etchant is a gas or plasma.

Typically the etchant is sulphur hexa-fluoride.

Typically the method includes, controlling the etching process by varying etching parameters including at least one of:
a) a ratio of the etchant to the passivant;
b) a gas flow for at least one of the etchant and the passivant; and,
c) a pressure for at least one of the etchant and the passivant.

Typically the ratio is in the range of 0.25 to 0.60.

Typically the pressure of at least one of the etchant and the passivant is in the range of 0 to 26.7 Pa (0 to 200 mT).

Typically the pressure of at least one of the etchant and the passivant is in the range of 0.67 to 8.0 Pa (5 to 60 mT).

Typically the etchant is supplied at a flow rate in the range of at least one of:
a) 0 to 200 sccm; and,
b) 40 to 120 sccm.

Typically the passivant is supplied at a flow rate in the range of at least one of:
a) 0 to 200 sccm; and,
b) 10 to 80 sccm.

Typically the method includes:
a) applying a mask material to the substrate; and,
b) selectively exposing the mask material to radiation to thereby form the mask.

Typically the mask material is at least one of:
a) an organic photo-resist;
b) a polymer mask; and,
c) a crosslinked epoxy resin.

Typically the mask material is Su-8.

Typically the method includes, performing post-etch processing.

Typically the method includes, chemically sharpening the projections.

Typically the method includes, sharpening the projections by:
a) forming a silicon dioxide layer on the projections; and,
b) removing the silicon dioxide layer.

Typically the method includes forming a silicon dioxide layer on the projections by heating the projections in an oxygen rich environment.

Typically the method includes heating the projections to a temperature of greater than 1000° C.

Typically the method includes removing the silicon dioxide using 10% HF.

Typically the method includes, applying a coating to the projections.

Typically the coating is a metallic coating.

Typically the method includes using sputter deposition to deposit:
a) an adhesion layer; and,
b) a metallic layer on the adhesion layer.

Typically the adhesion layer includes chromium.

Typically the metal layer includes gold.

Typically the method further includes coating the projections with a material.

Typically the material is a therapeutic agent.

Typically the patch has a surface area of approximately 0.4 $cm^2$.

Typically the projections have a density of between 1,000-30,000 projections/$cm^2$.

Typically the projections have a density of 20,000 projections/$cm^2$

Typically the projections have a length of between 10 to 200 μm.

Typically the projections have a length of 90 μm

Typically the projections have a radius of curvature of greater than 1 μm.

Typically the projections have a radius of curvature greater than 5 μm.

Typically the projections include a support section and a targeting section.

Typically the targeting section has a diameter of less than at least one of:
a) 1 μm; and,
b) 0.5 μm.

Typically a length for the targeting section is at least:
a) less than 0.5 μm; and,
b) less than 1.0 μm; and,
c) less than 2.0 μm.

Typically a length for the support section is at least one of:
a) for epidermal delivery <200 μm;
b) for dermal cell delivery <1000 μm;
c) for delivery to basal cells in the epithelium of the mucosa 600-800 μm; and,
d) for lung delivery of the order of 100 μm in this case.

In a second broad form the present invention provides a method of producing projection on a patch, the method including:
a) providing a mask on a substrate, the mask including an organic photo-resist material; and,
b) etching the substrate using an etchant and a passivant to thereby control the etching process and form the projections.

In a third broad form the present invention provides a method of controlling an etching process to thereby produce projections on a patch, the method including:
a) etching the substrate using an etchant; and,
b) using a passivant other than oxygen to control the etching.

In a fourth broad form the present invention provides a method of producing projection on a patch, the method including:
a) providing a mask on a substrate; and,
b) etching the substrate using an etchant and a passivant to thereby control the etching process and form the projections, wherein the passivant includes at least one of:
i) a per-fluoride hydrocarbon; and,
ii) a fluorinated olefine;
iii) Octafluorocyclobutane;
iv) Perfluoroisobutene; and,
v) $C_4F_8$.

BRIEF DESCRIPTION OF THE DRAWINGS

An example of the present invention will now be described with reference to the accompanying drawings, in which:—

FIGS. 23A and 23B are secondary electron images of examples of projection arrays having coated and uncoated projections respectively;

FIGS. 24A and 24B are examples of CryoSEM images illustrating the penetration of skin by the projections on a patch;

FIGS. 25A and 25B are examples of CryoSEM images illustrating the penetration of skin by the projections on a patch;

FIGS. 26A and 26B are secondary electron images of a patch after application to mouse ear skin.

DETAILED DESCRIPTION OF THE PREFERRED EMBODIMENTS

An example of a device for delivering material to targets within a body will now be described with reference to FIGS. 1A to 1F.

In this example, the device is in the form of patch 100 having a number of projections 110 provided on a surface 121 of a substrate 120. The projections 110 and substrate 120 may be formed from any suitable material, but in one example, are formed from a silicon type material. The projections may be solid, non-porous and non-hollow, although this is not essential.

In the example shown, the patch has a width W and a breadth B with the projections 110 being separated by spacing S.

Figure 1A:
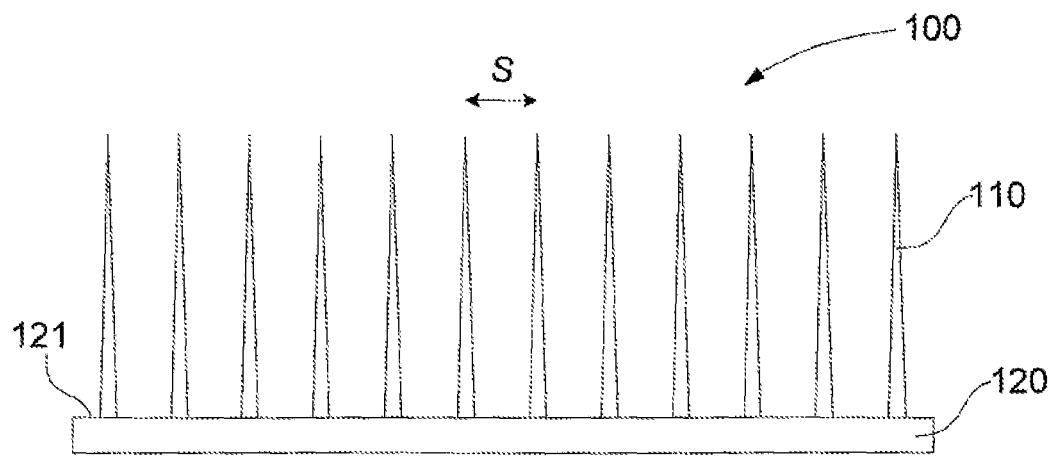
FIGS. 1A and 1B are schematic side and plan views of an example of device for delivery of material to targets within a body.
Figure 1B:
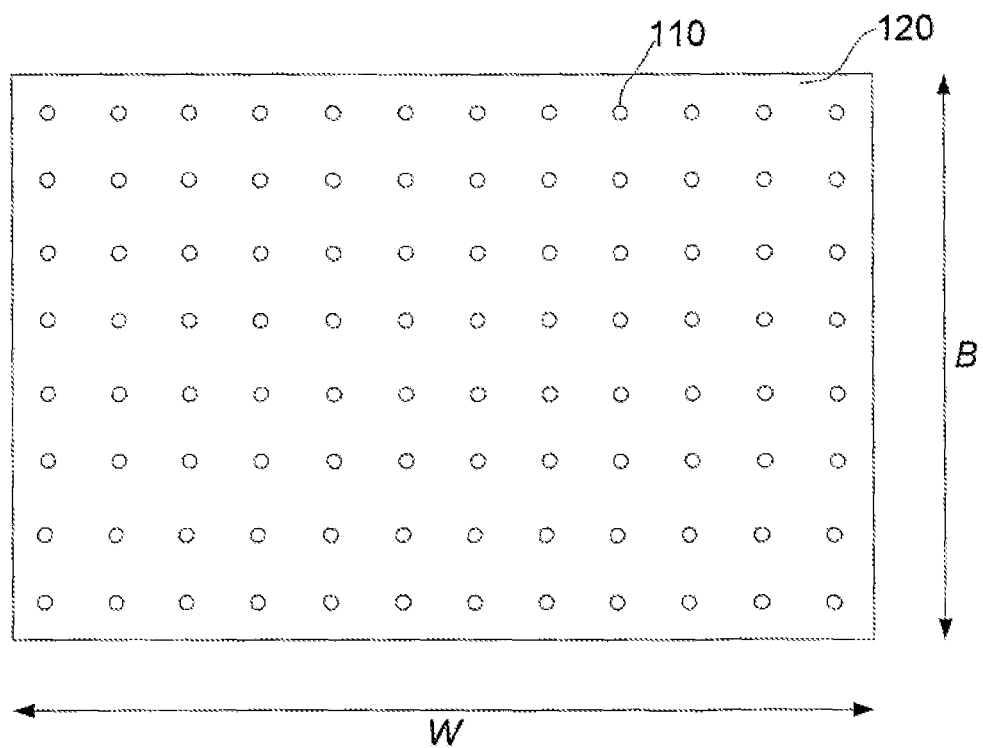
Figure 1C:
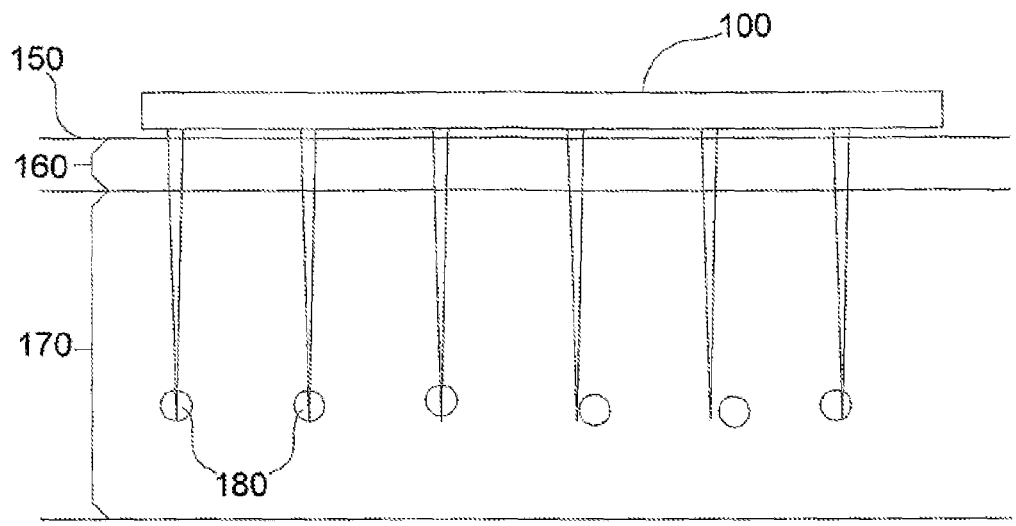
FIG. 1C is a schematic diagram of an example of the device of FIG. 1A in use.

In use, the patch 100 is positioned against a surface of a subject, allowing the projections to enter the surface and provide material to targets therein. An example of this is shown in FIG. 1C.

In this example, the patch 100 is urged against a subjects skin shown generally at 150, so that the projections 110 pierce the Stratum Corneum 160, and enter the Viable Epidermis 170 to reach targets of interest, shown generally at 180. However, this is not essential and the patch can be used to deliver material to any part or region in the subject.

Figures 1D, 1E, 1F:
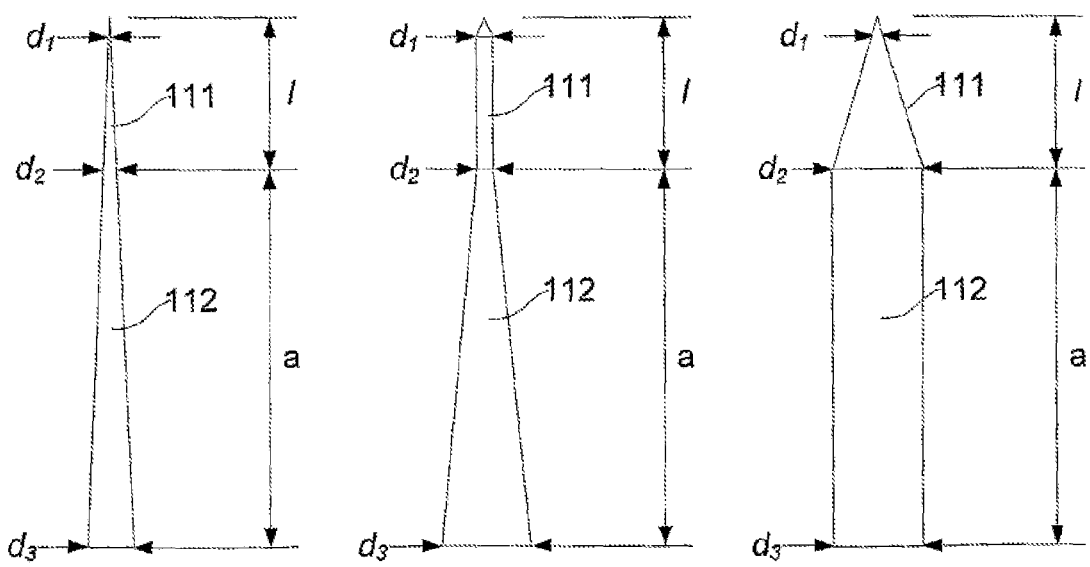
FIGS. 1D to 1F are schematic diagrams of examples of projections used in the device of FIG. 1A.

It will be appreciated that the projections can have a variety of shapes, and examples of suitable projection shapes are shown in more detail in FIGS. 1D, 1E and 1F.

In one example, the projection includes a targeting section 111, intended to deliver the material or stimulus to targets within the body, and a support section 112 for supporting the targeting section 111. However, this is not essential, and a single element may be used.

In the example of FIG. 1D, the projection is formed from a conically shaped member, which tapers gradually along its entire length. In this example, the targeting section 111 is therefore defined to be the part of the projection having a diameter of less than d.

In FIGS. 1E and 1F, the structure of the projection may vary along its length to provide a defined targeting section 111 with a designed structure. In the example of FIG. 1E, the targeting section 111 is in the form of a substantially cylindrical shape, such that the diameter $d_1$ is approximately equal to the diameter $d_2$, with a tapered support section, such that the diameter $d_2$ is smaller than the diameter $d_3$. In contrast, in the example of FIG. 1F, the targeting section 111 is in the form of taper such that the diameter $d_1$ is smaller than the diameter $d_2$, with a cylindrical support section, such that the diameter $d_2$ is substantially equal to the diameter $d_3$.

In general, the support section 112 has a length a, whilst the targeting section 111 has a length l. The diameter of the tip is indicated by $d_1$, whilst the diameter of the support section base is given by $d_3$.

In use, the device can be used to deliver material to specific targets within the body or more generally to the blood supply, or tissue within the body and the configuration of the device will tend to depend on its intended use.

Thus, for example, if the patch is configured so as to ensure material is delivered to specific targets such as cells, then it may be necessary to select a more specific arrangement of projections than if delivery is provided more generally to the blood. To achieve this, the device can be provided with a particular configuration of patch parameters to ensure specific targeting. The patch parameters can include the number of projections N, the spacing S between projections, and the projection size and shape. This is described in more detail in to co-pending application U.S. Ser. No. 11/496,053.

In one specific example, a patch having a surface area of approximately 0.16 cm² has projections provided at a density of between 1,000-30,000 projections/cm², and typically at a density of approximately 20,000 projections/cm². However, alternative dimensions can be used. For example, a patch for an animal such as a mouse may have a surface area of 0.32 to 0.48 cm², whereas as a patch for a human may have a surface area of approximately 1 cm². A variety of surface areas can be achieved by mounting a suitable number and arrangement of patches on a common substrate.

The projections typically have a length of between 10 to 200 µm and typically 90 µm with a radius of curvature of greater than 1 µm and more typically greater than 5 µm. However, it will be appreciated that other dimensions may be used.

If distinct targeting section and support sections are provided, the targeting section typically has a diameter of less than 1 µm and more typically less than 0.5 µm. The length of the targeting section is typically less than 100 µm, less than 10 µm and typically less than 5 µm. The length of the support section typically varies depending on the location of the target within the subject. Example lengths include less than 200 µm for epidermal delivery, less than 1000 µm for dermal cell delivery, 600-800 µm for delivery to basal cells in the epithelium of the mucosa and approximately 100 µm for lung delivery.

A process for the production of projections on a patch will now be described.

In one example, the process includes providing a mask on a substrate and etching the substrate using an etchant and a passivant to thereby control the etching process and form the projections.

The etchant is typically a compound formed from a group 16 element and a halide. In one example, the etchant contains sulphur and fluorine, and may therefore include sulphur hexafluoride ($SF_6$) or the like.

The passivant is typically a gas other than oxygen, and in particular typically includes a group 14 element and a halide. In one example, the passivant is a per-fluoride hydrocarbon such as octafluorocyclobutane ($C_4F_8$).

The use of suitable etchants and passivants other than oxygen allows for a high degree of control to be provided over the etching process. In particular, adjusting etch parameters such as the passivant to etchant ratio, the gas flow and the system pressure, this allows etching rates to be controlled. This in turn allows the degree to which the process is isotropic or anisotropic to be adjusted. By controlling the relative characteristics, this allows the shape of the resulting projections to be carefully controlled.

The mask may be provided on the substrate using any one of a suitable number of techniques. However, in one example, this is achieved by applying a mask material to the substrate and then selectively exposing the mask material to radiation to thereby form the mask. When passivants other than oxygen are used, the mask material can be formed from an organic photo-resist, such as a crosslinked epoxy resin based polymer. An example of such a material is Su-8 2000 supplied by MicroChem Corp, although other similar related materials can be used. Polymer masks are generally significantly easier to create and use, resulting in the process being significantly cheaper than when a hard mask, such as a metal mask is used.

Accordingly, the above described technique allows for the production of silicon projections to be completed using a combination of optical lithography and deep silicon etching. This allows the profile of the projections to be carefully controlled, thereby allowing projections suitable for use in a range of applications to be created.

Figure 2:
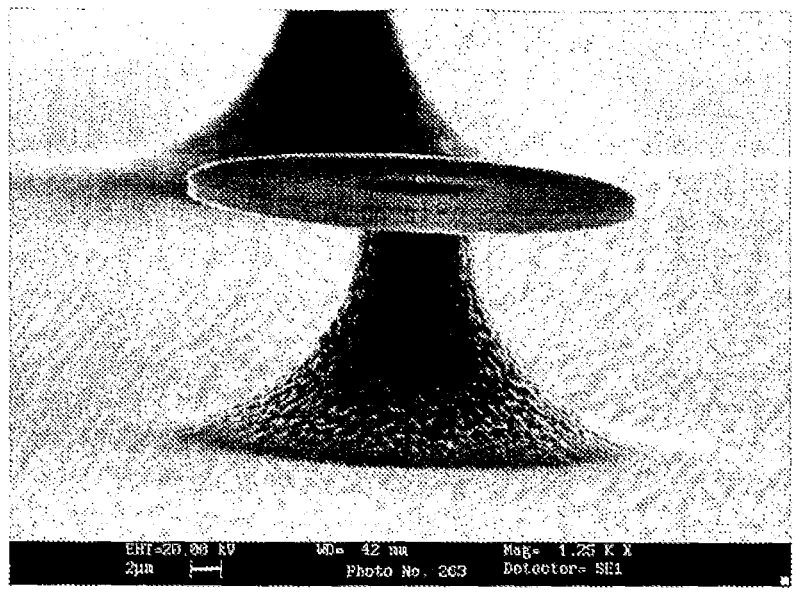
FIG. 2 is an example of a secondary electron image of a concave profiled projection.

Prior art techniques utilising fluorine/oxygen chemistry provide only extremely limited control over the etching process. This is in part due to the formation of a SiliconOxyFluoride layer on the surface of the wafer as part of the passivation process. Formation of the layer occurs rapidly and is difficult to control. Furthermore, the hardness of the layer means that it tends to interfere with the remainder of the etch process. As a result, it is generally only possible to produce projections having a concaved profile, which in turn results in a narrow tip that is thin and liable to breakage. A secondary electron image of an example of a concave profiled projection is shown in FIG. 2.

Figure 3:
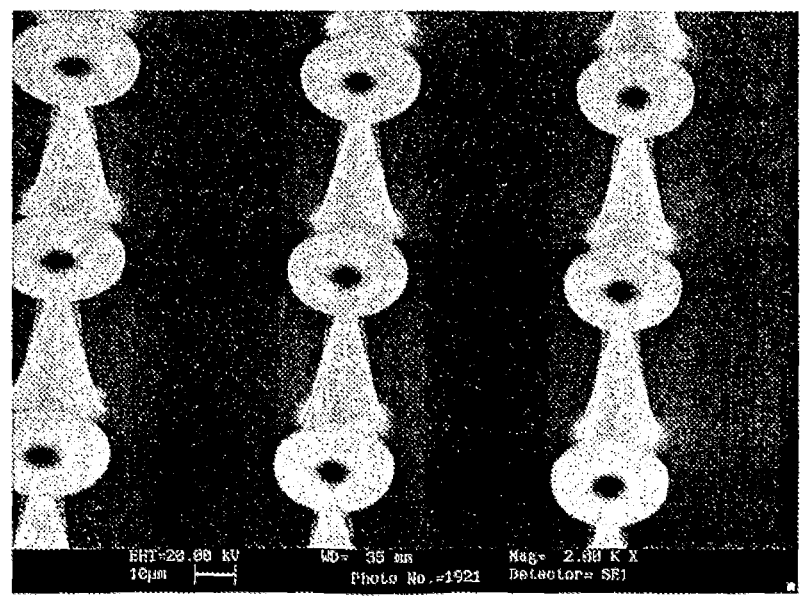
FIG. 3 is an example of a secondary electron image of a straight profiled projection.

In contrast to this, by using a suitable alternative passivant to thereby control the etching to process, this avoids the formation of a SiliconOxyFluoride layer, which in turn allows a greater control over projection shape to be achieved. In one example, this can be used to allow for a more straight profiled conical shape to be produced, an example of which is shown in FIG. 3. By virtue of the thicker tip shape, this provides for more robust projections which are more capable of delivery of material or stimulus to a desired target within a subject. Other shapes can also be provided for, as will be described in more detail below.

Further benefits are also obtained. In particular, the use of the above described passivants and etchants, allows an organic based photo-resists to be used as masks, instead of the metal required by the prior art. The organic based photo-resist masks are easier and cheaper to produce. Additionally, these can be of a reduced height as compared to the metal masks required in fluorine/oxygen based etching processes, which in turn provides further control over the resulting patch geometry.

In addition to the steps described above, following formation of the projections, one or more post-etch processing steps may be performed.

In one example, following formation of the projections, the projections undergo a chemical sharpening process. Chemical sharpening is performed so as to reduce the roughness of the projections, which can in turn enhance the ability of the projections to deliver material or stimulus to targets within the subject. Sharpening may be achieved in any one of a number of manners, but in one example, is achieved by forming a silicon dioxide layer on the projections and then subsequently removing the silicon dioxide layer. This process will be described in more detail below.

Figure 4:
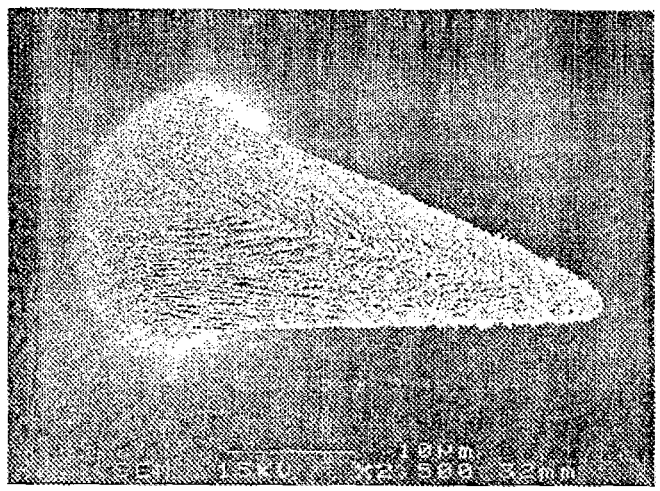
FIG. 4 is an example of a secondary electron image of a projection having a gold coating.

A further post-etch process that may be performed is to coat the projections. Any suitable coating may be used, and this can include coating the projections with a material to be delivered to the subject, as described for example in co-pending application AU-2007907092. Additionally, and/or alternatively, the projection may be coated with a metallic material such as gold. This can assist binding of other material to the projection, and can also improve surface properties to assist in material delivery to the subject. An example of a gold coated projection is shown in FIG. 4.

Figure 5A:
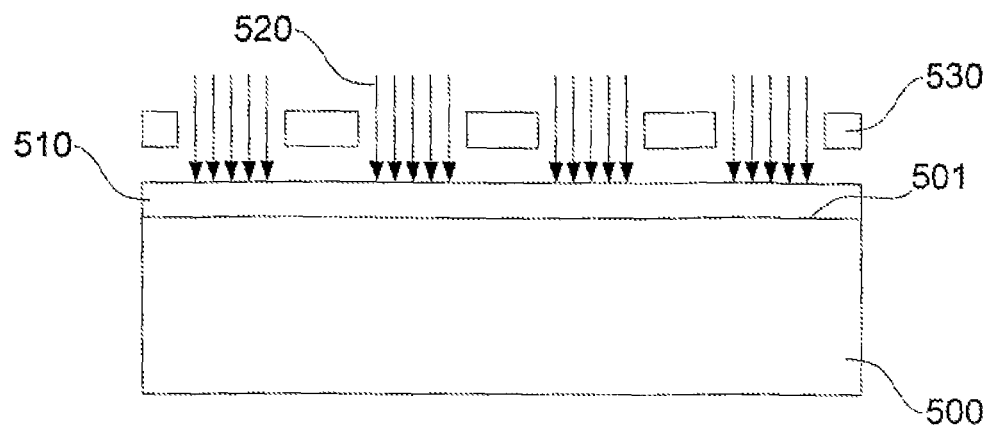
FIGS. 5A to 5C are schematic diagrams of an example of the steps in etching projections in a substrate.
Figure 5B:
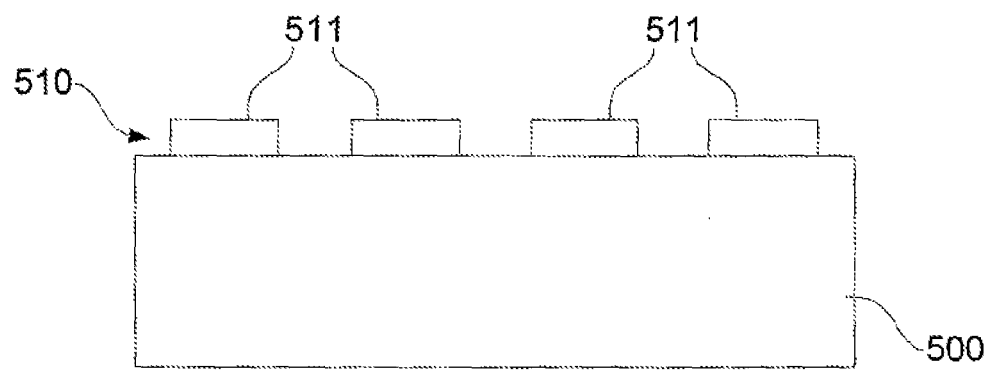

Examples of the process will now be described in more detail with reference to FIGS. 5A to 5C.

In this example, the first step is to produce a plasma etch mask. To achieve this, a suitable mask material, such as Su-8, which is a photoreactive polymer, is applied to a substrate 500, which in one example is 4 inch, 500 µm thick 100 silicon wafer. The substrate 500 is then spun at an appropriate speed to distribute polymer in a layer 510 over a surface 501 of the substrate 500. The spin speed is selected to control the thickness of the mask layer 510. In one example, to form a projection having a length in the region of 50-70 µm, the mask layer 510 has a thickness in the region of 7-8 µm. It will be appreciated that a thicker mask, such as up to 30 µm may be used.

The substrate 500 and mask layer 510 are optionally treated. This may be performed, for example to remove any excess solvent, which can be achieved by soft baking the substrate 500 and layer 510 for five minutes at 95° C.

Once suitably prepared, the mask layer 510 can be selectively exposed with radiation 520 to cause the exposed mask material to harden. In one example, this is achieved using a suitable photo-mask 530 and radiation source. Thus, exposure of the Su-8 film can be performed using chromium on quartz photo-mask and a Carl Suss MA6 mask aligner set to supply 10 mJ/second UV light. Typically complete cross-linking of the Su-8 polymer occurs after 1.8 seconds of exposure for 1 µm of Su-8 thickness, although longer exposure of up to 30 seconds can be used to ensure complete cross-linking of mask layers.

The substrate 500 and mask layer 510 may again be optionally treated, for example by baking for one minute at 95° C. This can be used to promote the formation and release of a Lewis Acids which aids the cross-linking process and formation of a straight sidewall profile for the mask.

The unexposed mask material can be removed using a suitable solvent. Thus, in the above, the uncross-linked Su-8 can be removed by developing in EC solvent (PGMEA) for two minutes. The complete removal of uncross-linked Su-8 can be confirmed by washing the wafer with IPA. If a white precipitated is observed (indicating uncompleted development) the wafer is replaced in the EC solvent for further 30 seconds. Development is completed until no white precipitated is observed upon washing with IPA. The excess IPA can be removed by blow drying with dry nitrogen gas.

Further treatment may then be performed, such as hard baking of the wafer 500 at 1000° C. for five minutes. This can be used to harden and remove residual developer and IPA for the Su-8 mask. At this stage in the process, the mask layer 510 includes a number of dots 511, as shown in FIG. 5B. The next stage in the process is the formation of projections by etching. In one example, this is achieved using plasma etching, which can be completed on an STS (Surface Technology Systems) ASE (Advanced Silicon Etch) system. In one example, this is achieved using $SF_6$ as the etch gas and $C_4F$. as the passivation gas, although as described above, other gases can be used.

Controlled continuous isotropic plasma etch process was complete with a plasma gas mixture of $SF_6$:$C_4F_8$ typically in the ratio range of 0.25 to 0.60. Vertical, horizontal and projection tip angle can be controlled to provide required projection profiles. This is achieved by ramping or varying the plasma gas condition throughout the etch process, by changing the rate of gas flow, pressure and $SF_6$: $C_4F_8$ ratios.

Figure 5C:
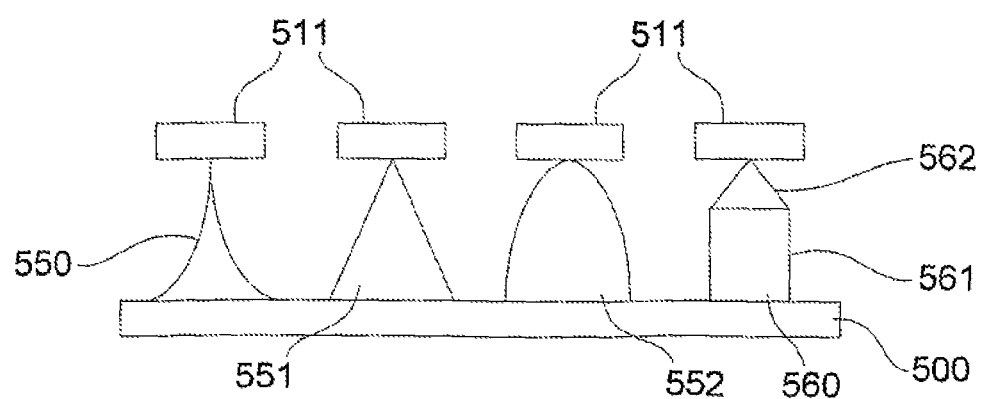
Figures 6A, 6B, 6C:
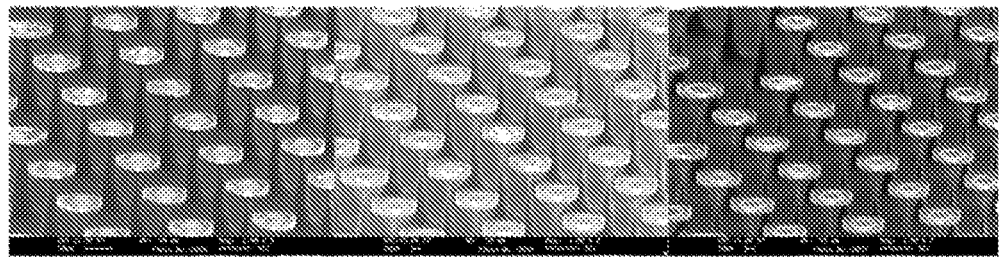
FIGS. 6A to 6C are examples of secondary electron images of projections produced using different etching times.

In one example, by performing a continuous etch for approximately 30-60 minutes, projection profiles of concave to convex shapes can be achieved, as shown at 550, 551, 552 in FIG. 5C. Example projection profiles obtained in performing etching under similar conditions, but for different time periods are shown in FIGS. 6A to 6C, which show the result of etching for 40 mins, 45 mins and 50 mins respectively. In this instance, the images highlight how the longer etching time results in a narrower taller projection, as would be expected by the increased amount of etching.

A further alternative, etching can be performed in multiple stages to provide additional control. In one example, a continuous etch is performed for approximately 30-60 minutes, with a subsequent etch being performed for a further 15-30 minutes. This allows a projection 560 having a column shaped supporting section 561 and a conical tip 562 to be produced, as shown in FIG. 5C.

In one example, the profile of the projection can be formed by altering etching parameters, such as the $SF_6$:$C_4F_8$ ratio, pressures, or the like, between the different etch steps.

Additionally, the wafer 500 can be removed from the ASE system, allowing the wafer and/or passivant to react with the ambient atmosphere. This can alter the effect of the passivant, thereby altering the profiles that can be produced.

The ability to pause the etching process allows further control over the etching process. For example, the etching can be performed to near completion, with the process then being halted to allow the wafer or patches to be examined to determine the amount of etching required to complete the process. The process can then be resumed and completed.

Pausing the etching process can be performed as the passivant binds only relatively weakly to the silicon surface. Consequently, even when the passivant has reacted with the ambient air outside the etching system, the passivant can still be removed when etching recommences. In contrast, in fluorine/oxygen based etching techniques, the passivant binds strongly to the silicon surface through covalent bonding. Consequently, when the wafer is removed from the etching system an oxide layer is formed which cannot be controllably etched. This prevents fluorine/oxygen based etching process from being halted or paused to allow examination of the wafer, which in turn limits the degree of control that can be achieved.

This effect is particularly exacerbated when etching narrow projections, as the etching has a faster effect as the projection narrows, and the etch nears completion. As a result, when etching narrow projections using a fluorine/oxygen based etching approach, over etching often occurs, resulting in projections that are too narrow and hence fragile to use. This renders the resulting patches useless, which in turn leads to increased manufacturing costs.

Figure 7:
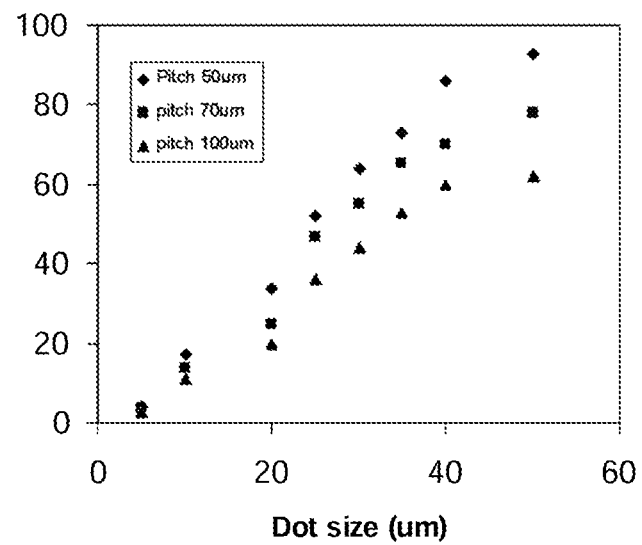
FIG. 7 is a graph illustrating an example of the effect of mask dots size and array pitch on etch depth.

The achievable height of the projections is dependent on a number of factors, such as the size and pitch (separation) of mask dots. An example of the effect of mask dots size and array pitch on etch depth is shown in FIG. 7. To form projections having a height in the region of 70 µm, the dots are typically formed with a diameter in the region of 7-8 µm. This is a smaller dot size than is typically required in a fluorine/oxygen based plasma etching technique.

Figure 8A:
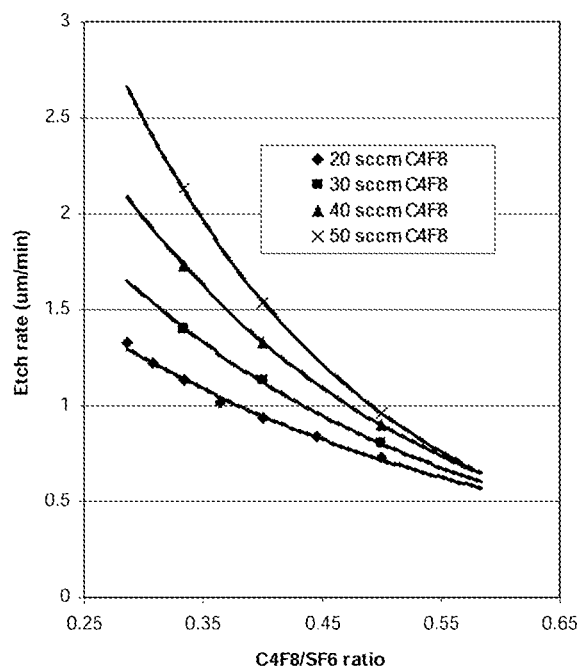
FIGS. 8A to 8C are graphs illustrating examples of the variation in vertical etch rates depending on $C_4F_8:SF_6$ ratios, gas flow rates and gas pressures respectively.
Figure 8B:
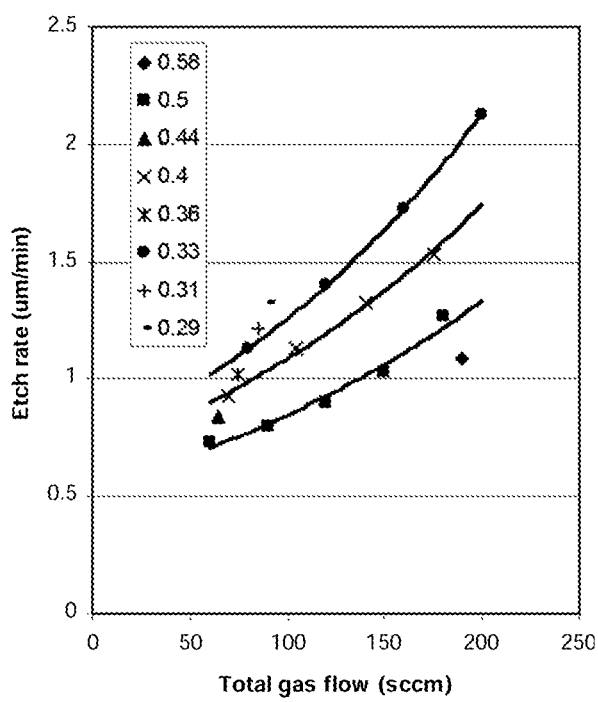
Figure 8C:
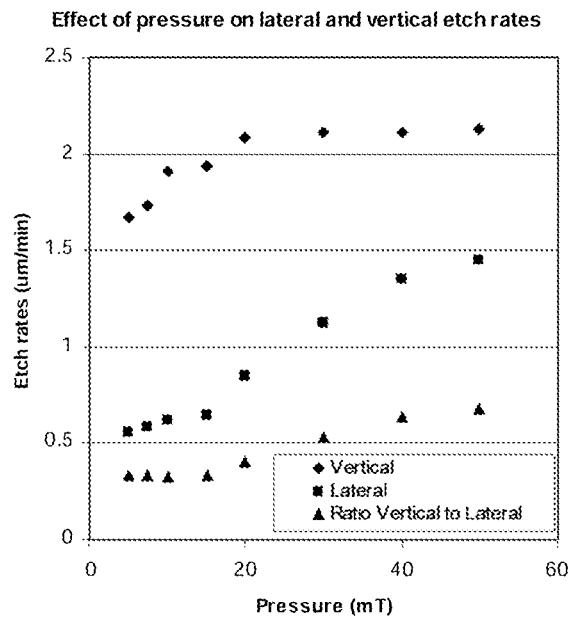

Additionally, plasma conditions effect projection profile control such that vertical silicon etch to rates decrease with increasing $C_4F_8$:$SF_6$ ratios, lower gas flow rates and low gas pressures as shown in FIGS. 8A to 8C.

Figure 9:
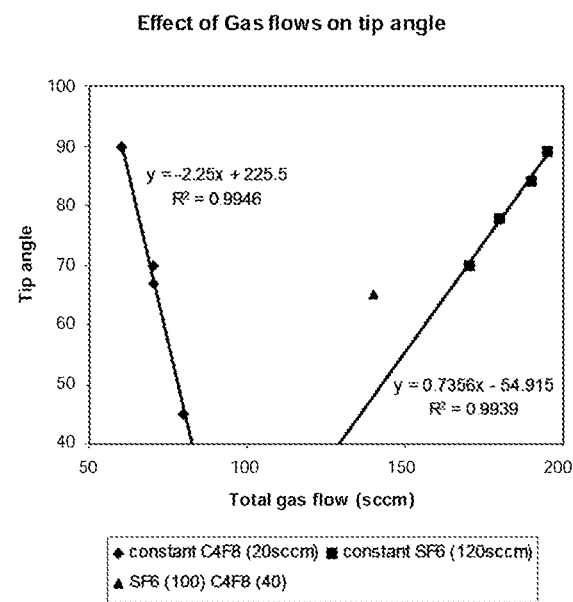
FIG. 9 is a graph illustrating an example of the effect of gas flow rates on projection tip angle.
Figure 10:
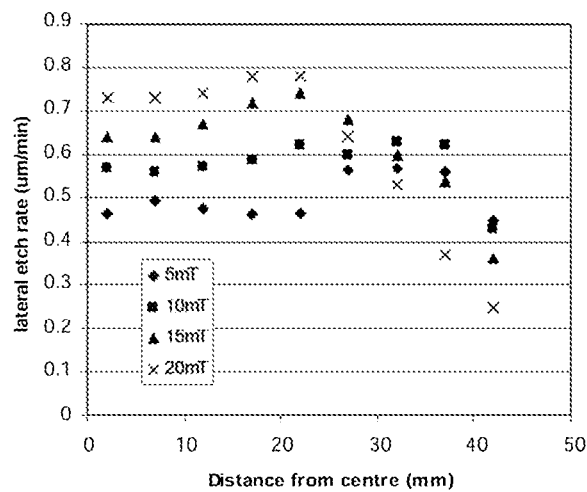
FIG. 10 is a graph illustrating an example of the effect of system pressure on lateral etch rates.
Figure 11:
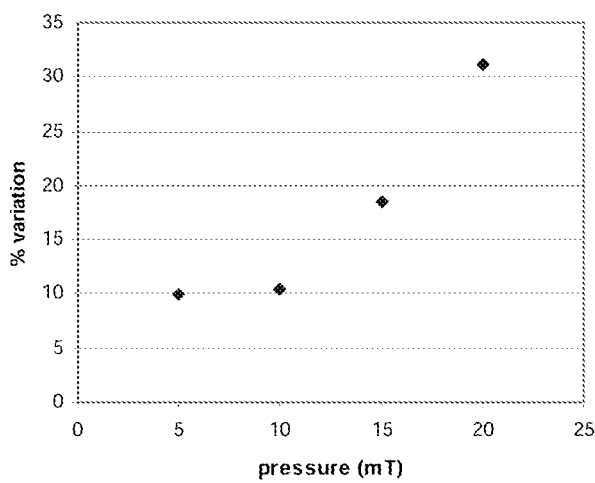
FIG. 11 is a graph illustrating an example of the effect of system pressure on etch uniformity.

Similarly lateral etch rates are effected, such that by increasing $C_4F_8$:$SF_6$ ratios results in a more anisotropic etch. By increasing total gas flow or system pressure an increased isotropic etch is observed, producing a more concave shaped of projection. The effect of gas flow rates on tip angle is shown in FIG. 9, with the effect of over pressure on lateral etch rates being shown in FIG. 10. FIG. 11 is a graph illustrating an example of the effect of system pressure on etch uniformity. This illustrates that in general a lower pressure of below 1.3 Pa (10 mT) is preferred to ensure good etch uniformity.

Figure 12:
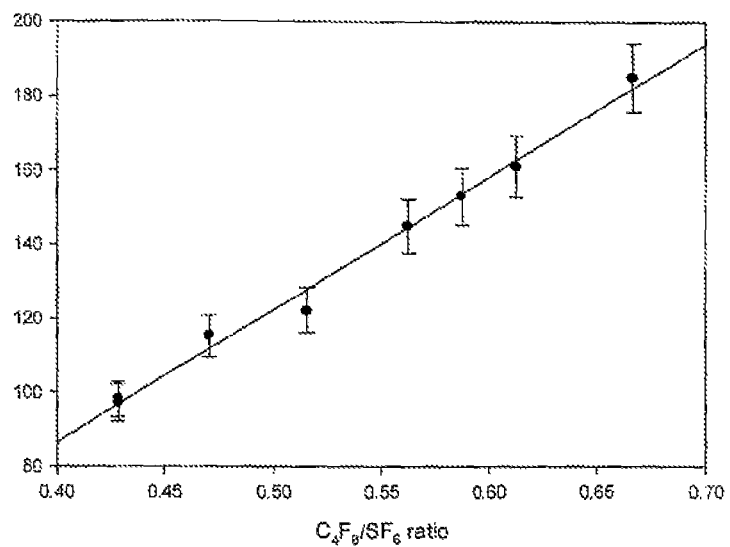
FIG. 12 is a graph illustrating an example of the effect of $C_4F_8:SF_6$ ratio on projection length.

FIG. 12 is a graph of the effect of $C_4F_8$:$SF_6$ ratio on projection length for etching performed using a 50 µm dot 70 µm pitch mask, at 0.3 Pa (2.5 mT), total flow rate 100 sccm and power 800 watts. This illustrates that as the $C_4F_8$:$SF_6$ ratio increases, so does the projection length that can be achieved.

Typically etchant is supplied at a flow rate in the range of 0 to 200 sccm (standard centimeter cube per minute), and more typically in the range of 40 to 120 sccm. Passivant may be supplied at a flow rate in the range of 0 to 200 sccm, and more typically in the range of 10 to 80 sccm.

Accordingly, by varying etch parameters such as the passivant to etchant ratio, the gas flow and the system pressure, this allows projection heights and profiles to be well defined. Additionally, by appropriate selection of etch parameters, the bullseye effect can be dramatically reduced when compared to fluorine/oxygen etches, thereby increasing the amount of useable patches that can be obtained from a etching process, which in turn increases the cost effectiveness of the process.

In one example, to obtain greater projection lengths, a conventional switched BORSH process can be performed. However, this is not essential and may depend on the system being used to perform the etching process.

Following completion of the etching, the etch mask can be removed and the silicon wafer chemical cleaned. This can be performed using an oxygen plasma and washing of silicon wafer in micro-strip (concentrated $H_2SO_4$ peroxide mixture).

Sharpening of the projections can be achieved via the formation of a silicon dioxide layer on the projections by heating the projections in an oxygen rich environment. In one example, a 1-2 μm thick layer of thermal silicon dioxide is formed by heating at 1050° C. under oxygen for 24-48 hours. The oxide is subsequently removed using 10% HF and washing in distilled water.

Figures 13A, 13B, 13C:
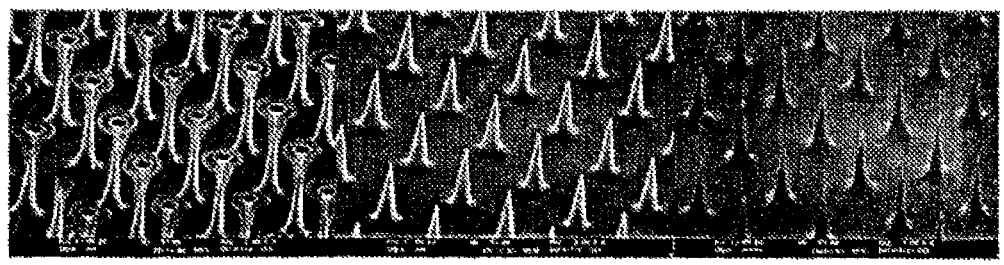
FIGS. 13A to 13C are examples of secondary electron images of projections following an $O_2$ plasma clean; an ultrasonic bath clean; and oxidation and HF sharpening, respectively.

Examples of the appearance of the projections after cleaning with $O_2$ plasma, after an ultrasonic bath clean and following oxidation and HF sharpening are shown in FIGS. 13A to 13C. These highlight how the cleaning and sharpening process result in smooth projections that are ideal for skin penetration.

Further optional treatment can be performed such as baking the wafer at 100° C. for 10 minutes to remove residual water.

Following this, gold coating can optionally be preformed using a DC sputter coating system. To achieve this, it is typical to clean the wafer surface using Argon gas sputtering before the depositing 50 nm of Chromium to act as an adhesion layer, followed by 100 nm of Gold.

A further benefit of the provision of a gold coating is to enhance the physical properties of the projections. Silicon tends to be brittle and as a result can fracture in use due to crack growth. However, the gold provide a soft ductile coating, which tends to absorb unwanted forces and impacts, thereby enhancing the resilience of the projections and reducing their failure rate in use.

The final wafer may be further cleaned using Argon gas sputtering.

Figure 14A:
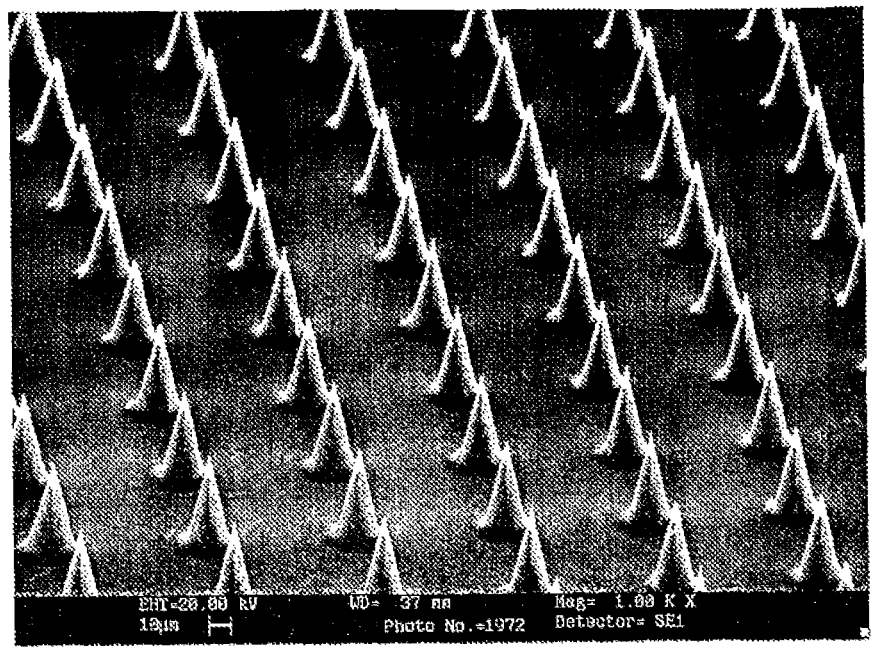
FIGS. 14A to 14C are secondary electron images of example patches including projections having lengths of 60, 100 and 150 µm, respectively; and, FIG. 14D is a secondary electron image of a projection patch after insertion into a subject.
Figure 14B:
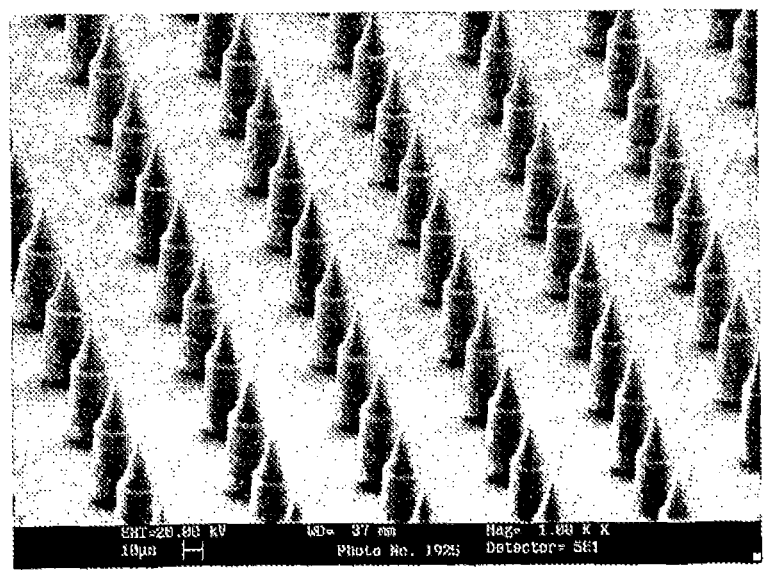
Figure 14C:
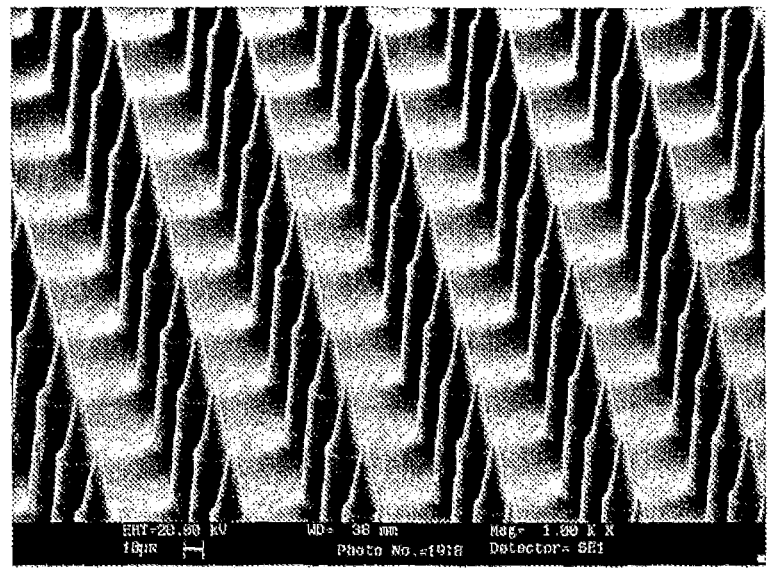
Figure 14D:
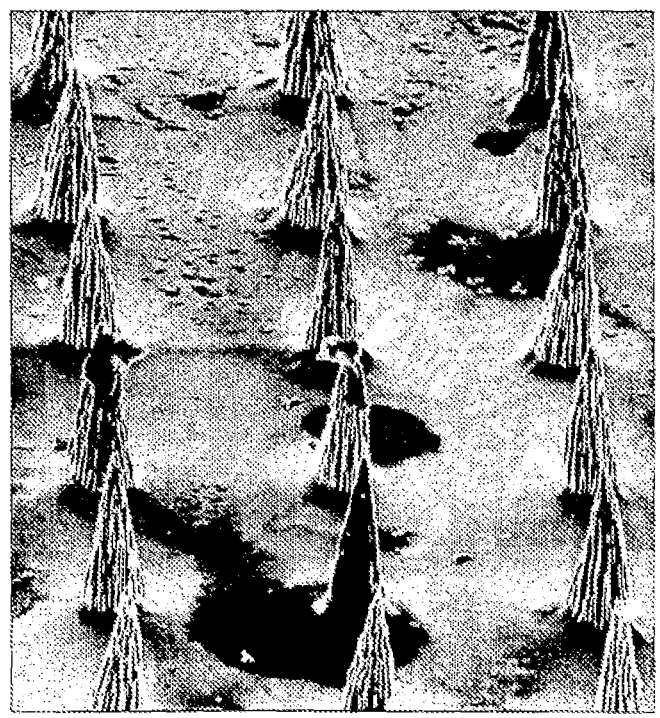

Examples of patches including 60, 100 and 150 μm length projections are shown in FIGS. 14A to 14C. An example of a projection patch after insertion into a subject is shown in FIG. 14D. It can be seen that the projections remain unbroken, highlighting that the projections are strong enough to remain intact after insertion into the subject.

The use of the processes described above can provide any one or more of a number of advantages.

For example, the use of a suitable passivation gas such as $C_4F_8$ allows the direct use of an organic photo-resist (for example Su-8). Su-8 is a high aspect ratio negative resist with good plasma etching properties (i.e. selectivity). A greatly increased selectivity of mask to silicon etching is found when using a passivant other than oxygen, such as $C_4F_8$. This allows for a simplification in manufacturing by reducing the number of process steps. Firstly the need for deposition of a hard etch mask is removed (no deposition of metals or dielectric required), secondly etching of the hard mask not required and thirdly removal photo-resist not necessary.

Su-8 is suitable for use in both anisotropic and isotropic etching. Using Su-8 as an etch mask provides a considerable reducing in production costs and time compared to prior art processes.

Using a passivation gas such as $C_4F_8$ allows a greater control over projection tip profiles to be provided. The use of oxygen as a passivation, gas unless employed in a cryo ICP system, will produce a concave profile. However, cryo ICP systems are generally expensive to operate and maintain, thereby making this technique unsuitable for use on a mass scale. Using $C_4F_8$ as a passivation gas, projections with profiles of concave, flat and convex form can be produced. The use of parameter ramping allows a high degree of tip profile control to be maintained.

Additionally, etching can be paused, allowing additional control over the etching process. This can be used to allow a range of different projection profiles to be produced, as well as to control termination of the etching process more accurately.

The use of fluorocarbons, such as $C_4F_8$ also reduces the impact of the bullseye effect, thereby increasing the amount of useable patches resulting from the etching process.

Chemical sharpening and surface morphology changes to silicon projection tips. Chemical sharpening to <10 nm tip diameter can be achieved, allowing for easier penetration of the stratum corneum with less pressure being required.

Wet and dry oxidation sharpening methods can be used. Morphological differences have been observed between wet and dry oxidation conditions consequently smooth or porous surface structure can be produced respectively. Porosity can also be further increased using electrochemical methods.

Gold can be used as an adhesion layer for delivery of DNA and biological materials with using the projections. This can also enhance the physical properties of the projections, thereby reducing their failure rate.

Accordingly, the above described process provides for the more efficient and cost effective manufacture of projections by plasma etching, as well as enabling greater control over the etching process, to allow specific projection profiles to be created.

A number of example projection shapes are shown in FIGS. 15A, 15B, 16A, and 16B.

Figure 15A:
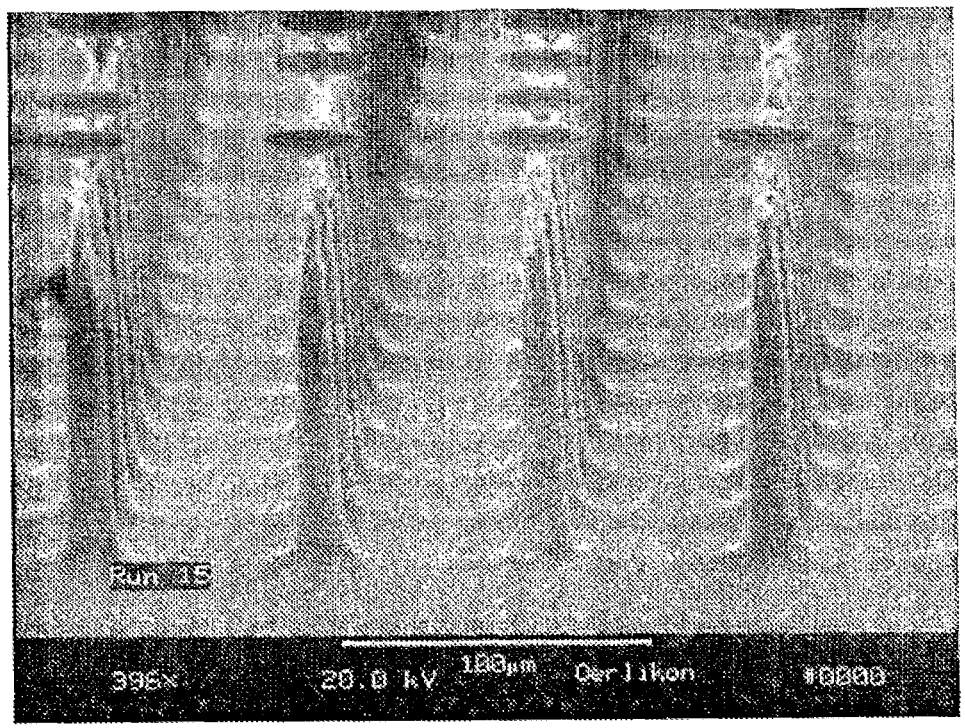
FIGS. 15A and 15B are examples of secondary electron images of projections obtained using a high rate Oerlikon etching system.
Figure 15B:
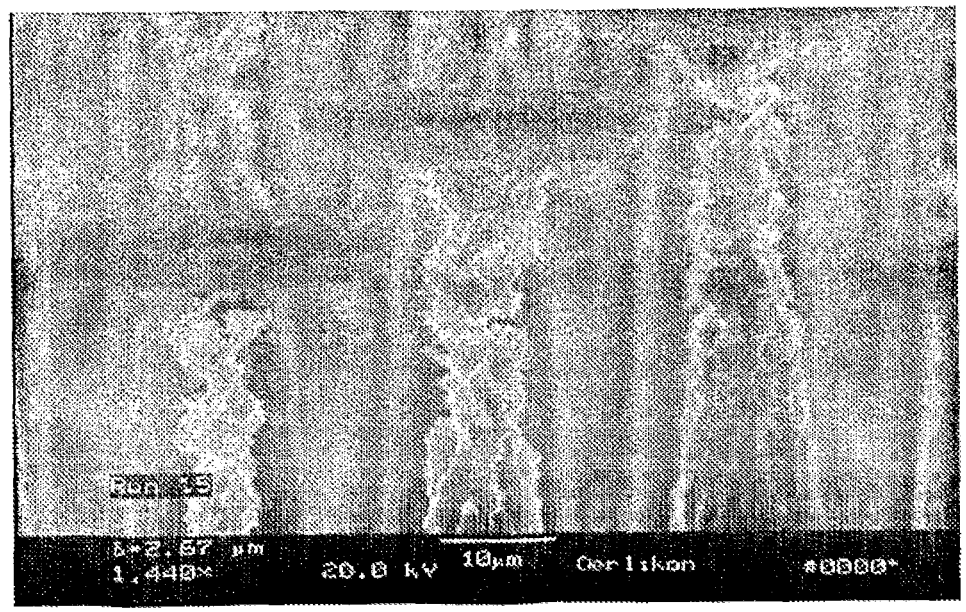

In the examples of FIGS. 15A and 15B, etching is performed as a two step process, using a $SF_6:C_4F_8$ ratio 2.5 for the first step and a $SF_6:C_4F_8$ ratio 1.2 for the second step. Both steps are performed at 2000 watts, 200 sccm total gas flow and 26.6 Pa (200 mT) pressure, using an Oerlikon etching system, which typically can etch at higher rates that the STS ASE system discussed above. In these examples a grainy structure is present at the top of the projections due to excess HF in the chamber.

Figure 16A:
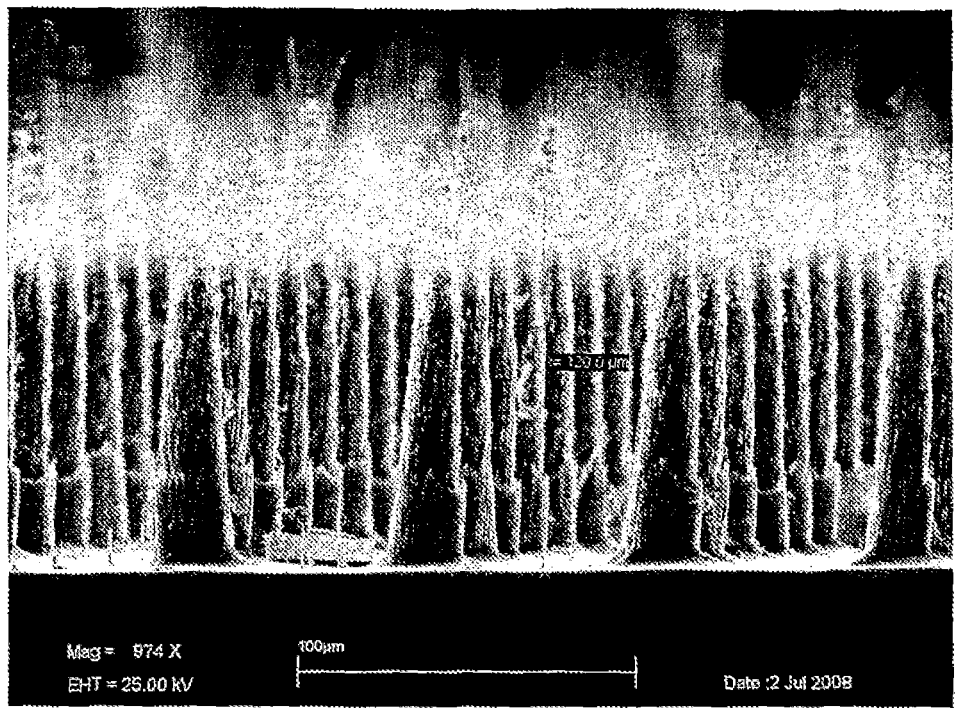
FIGS. 16A and 16B are examples of secondary electron images of projections obtained using a high rate STS etching system.
Figure 16B:
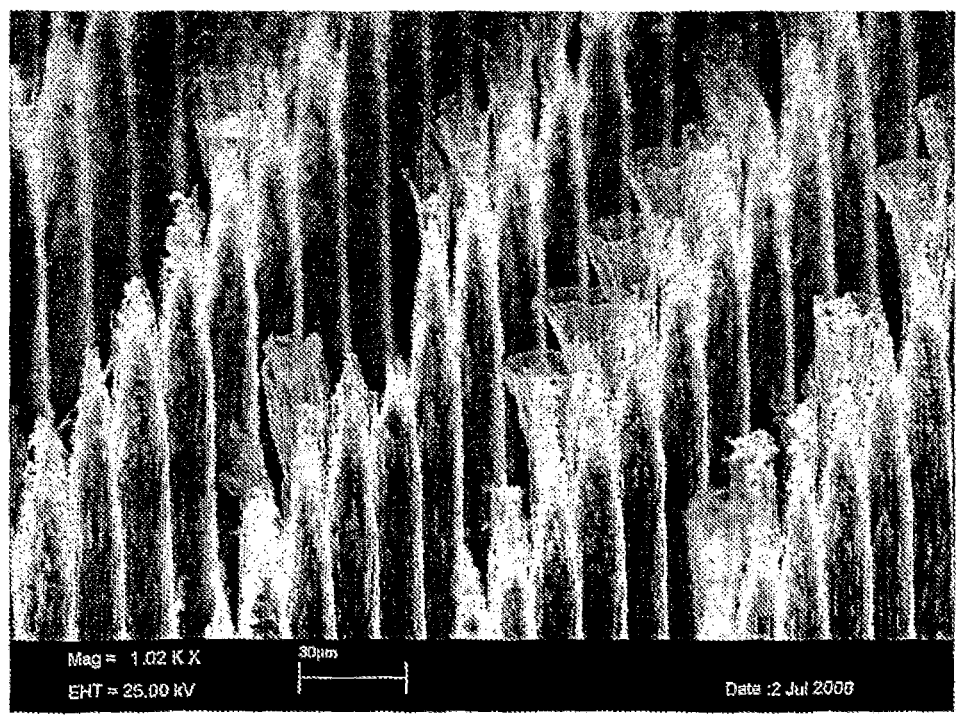
Figure 17:
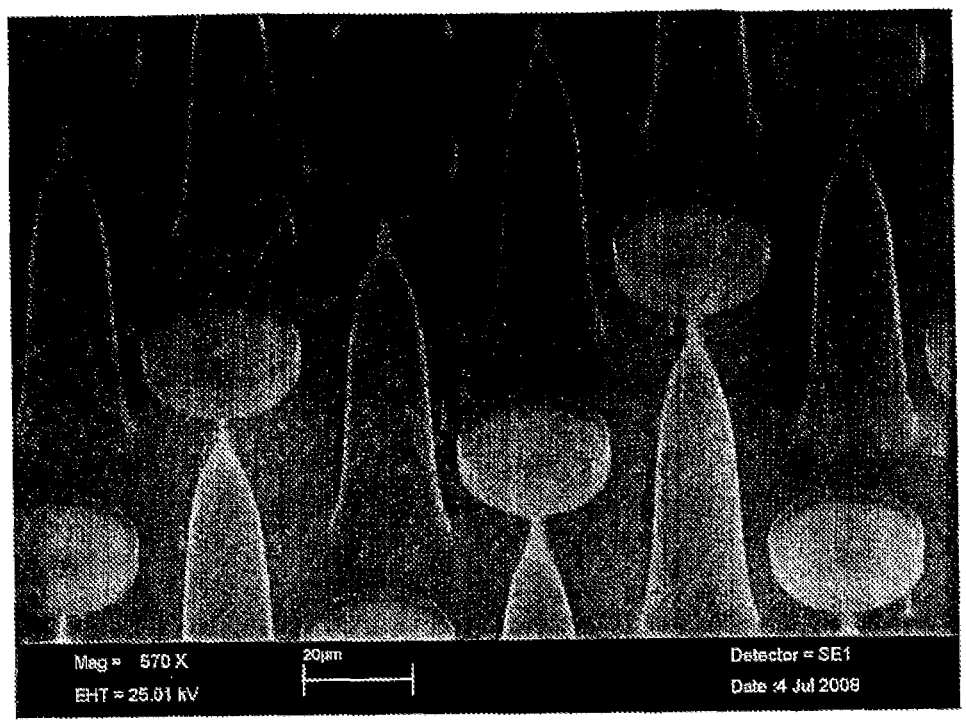
FIG. 17 is an example of a secondary electron images of projections obtained using a lower system pressure and power.

FIGS. 16A and 16B show similar results are obtained for a high rate STS etch. In this example, the projections have a length of 120 μm. The creation of a grainy structure can be reduced either by using a lower system power and pressure, which results in the smooth shaped projections shown in FIG. 17. However, in this example, the reduced pressure and power results in a shorter projection having a length of 80 μm, for similar etching parameters.

Example patch configuration produced using the above described etching techniques will now be described with reference to FIGS. 18 to 22.

Figure 18A:
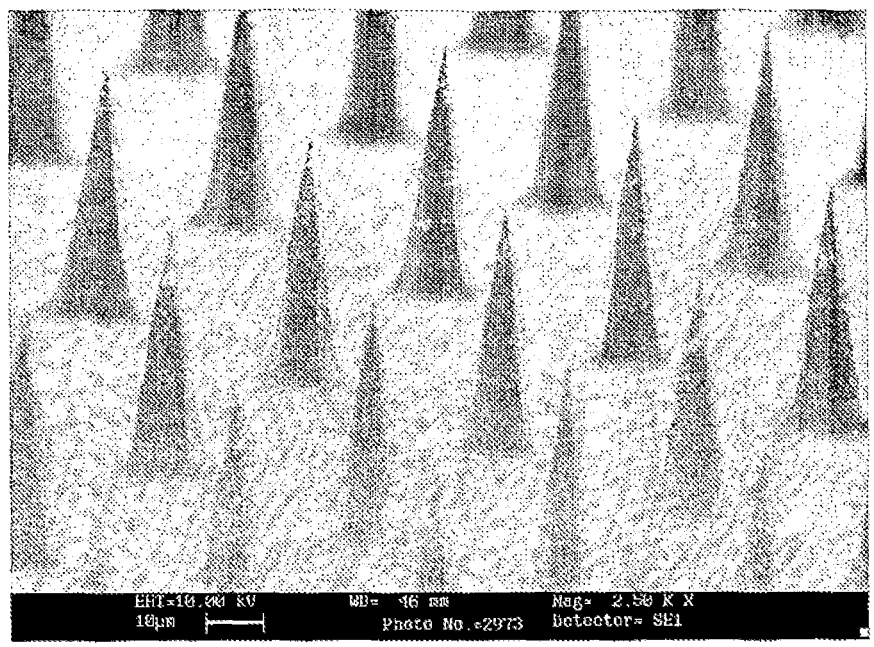
FIGS. 18A to 18E are secondary electron images of examples of projections having a conical straight edge profile.
Figure 18B:
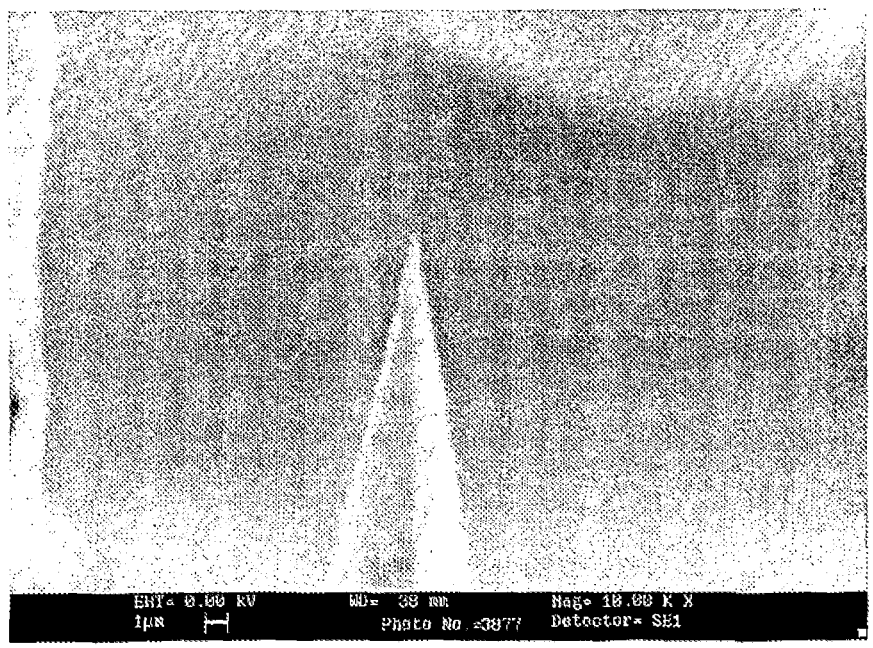
Figure 18C:
Figure 18D:
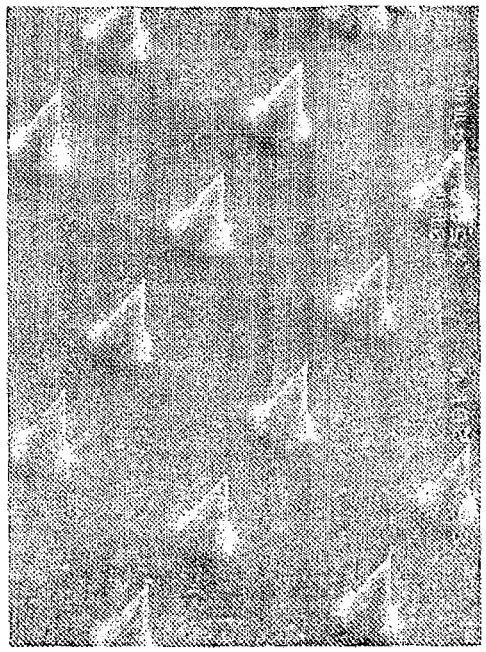
Figure 18E:
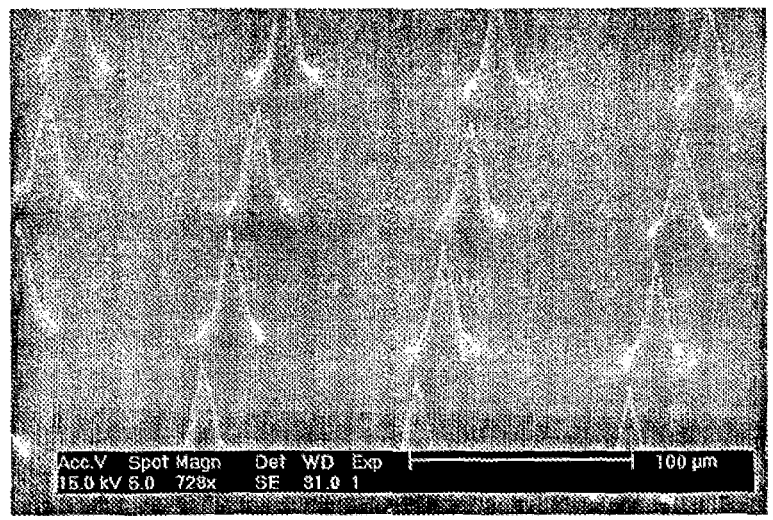

In the example of FIGS. 18A and 18E, a single stage etching process is used to produce projections having a conical shape.

For the example of FIGS. 18A and 18B, the etching parameters are broadly as set out below, resulting in projections having a length of approximately 50-70 μm depth, sub-micron sharp, 3-to-1 base to length aspect ratio, with a straight edge profile:

Etch mask 30 μm dot with 70 μm pitch;
Resist: Su8-5 spun to give 10 μm thickness
Etch: 36 sccm $C_4F_8$ passivant, 64 sccm $SF_6$ etchant, pressure 0.3 Pa (2.5 mT), power 800 watts coil, 20 watts platen
time 50 minutes.

A similar single stage etching process can be used with different etching parameters to produce projections have dimensions of 30 µm length, 70 µm spacing; 50 µm length, 70 µm spacing; and 70 µm length, 100 µm spacing, as shown in FIGS. 18C to 18E, respectively. It will be appreciated from this that a range of different conical projections can be produced and that these are for the purpose of example only.

Figure 19A:
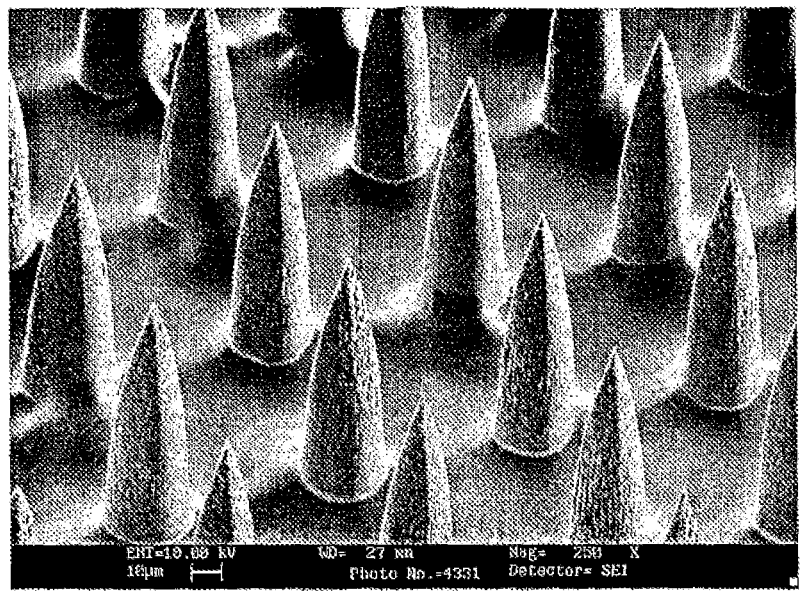
FIGS. 19A and 19B are secondary electron images of examples of projections having a conical convex edge profile.
Figure 19B:
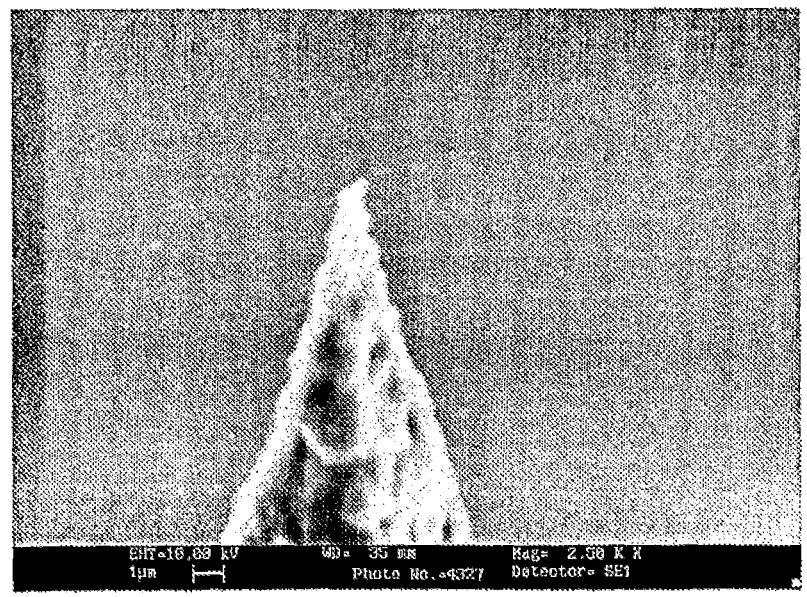

In the example of FIGS. 19A and 19B, a single stage etching process is used to produce projections having a conical shape, with a convex profile edge. In this example, using the etching parameters set out below, the projections typically have a length of approximately 150 µm, sub-micron sharp, 5-to-1 base to length aspect ratio, with a convex profile:
Etch mask 50 µm dot with 70 µm pitch
Resist: Su8-25 spun to give 25 µm thickness
Etch: gases 37 sccm $C_4F_8$ passivant, 63 sccm $SF_6$ etchant,
pressure 0.3 Pa (2.5 mT),
power 800 watts coil, 20 watts platen
time 2 hours 15 minutes In the examples of FIGS. 20A to 20E, a two stage etching process is used to produce stepped projections having a cylindrical base and conical shaped tip.

Figure 20A:
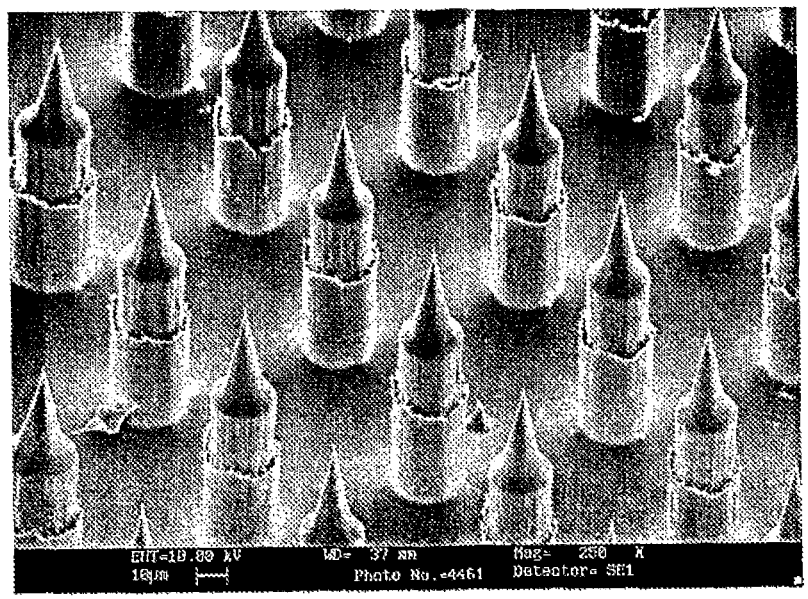
FIGS. 20A to 20E are secondary electron images of examples of projections having a stepped profile.
Figure 20B:
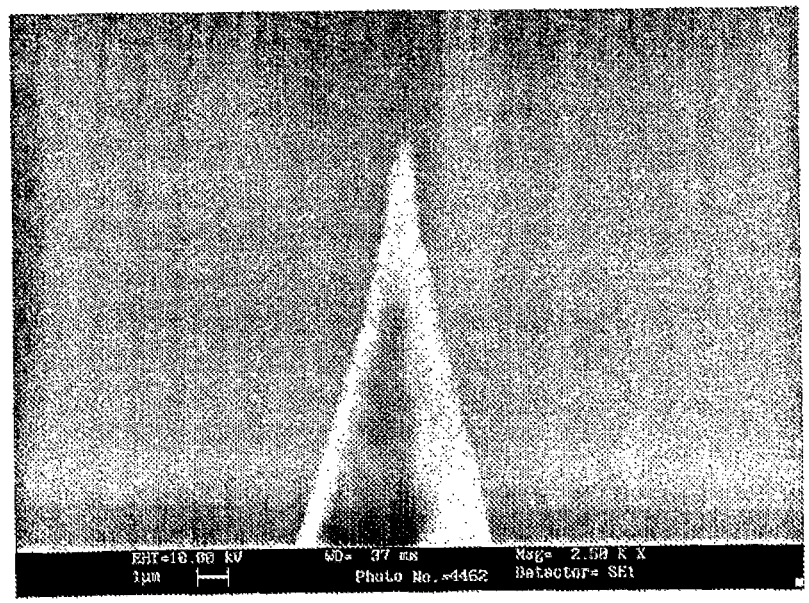
Figure 20C:
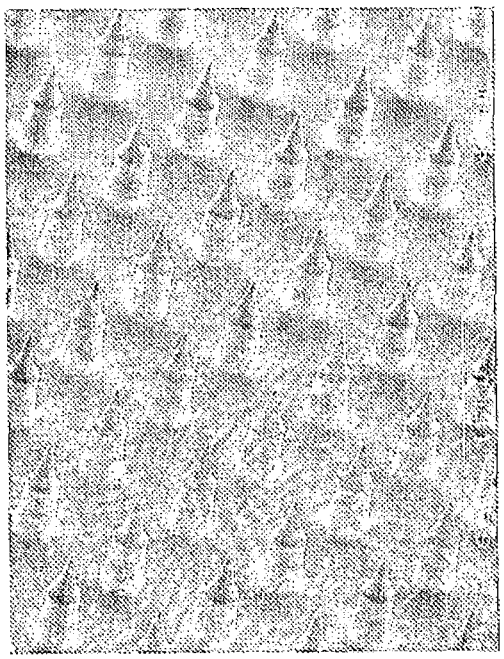
Figure 20D:
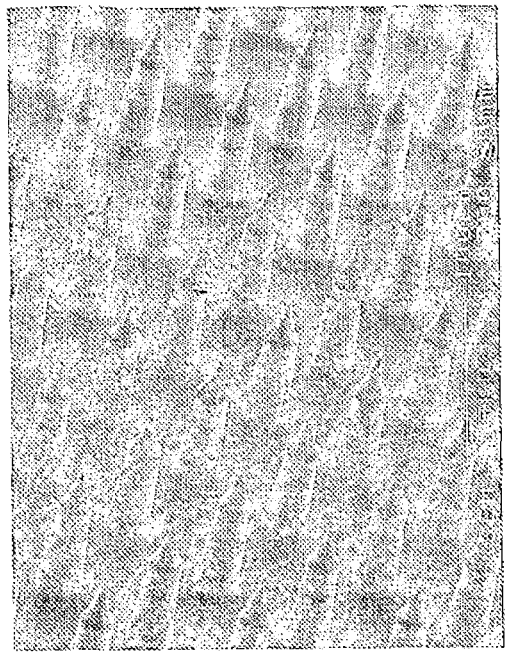
Figure 20E:
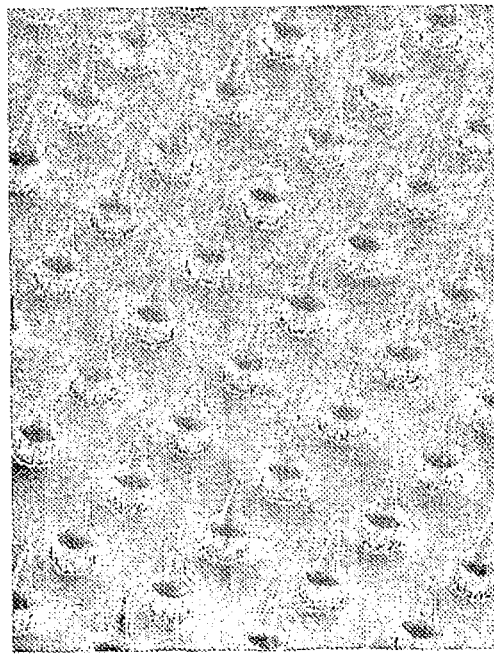

For the example of FIGS. 20A and 20B, the etching parameters are broadly as set out below, resulting in projections having a length of approximately 150 µm depth, hyper sharp, 5-to-1 base to length aspect ratio:
Etch mask 30 µm dot with 70 µm pitch
Resist: Su8-5 spun to give 10 µm thickness
Etch: gases 36 sccm $C_4F_8$ passivant, 64 sccm $SF_6$ etchant,
pressure 0.3 Pa (2.5 mT),
power 800 watts coil, 20 watts platen
time 50 minutes
1 hour conventional ASE switched etch In the examples of FIGS. 20C to 20E, alternative parameters are used to produce projections having lengths of 80 µm, 110 µm, and 65 µm respectively.

Figure 21:
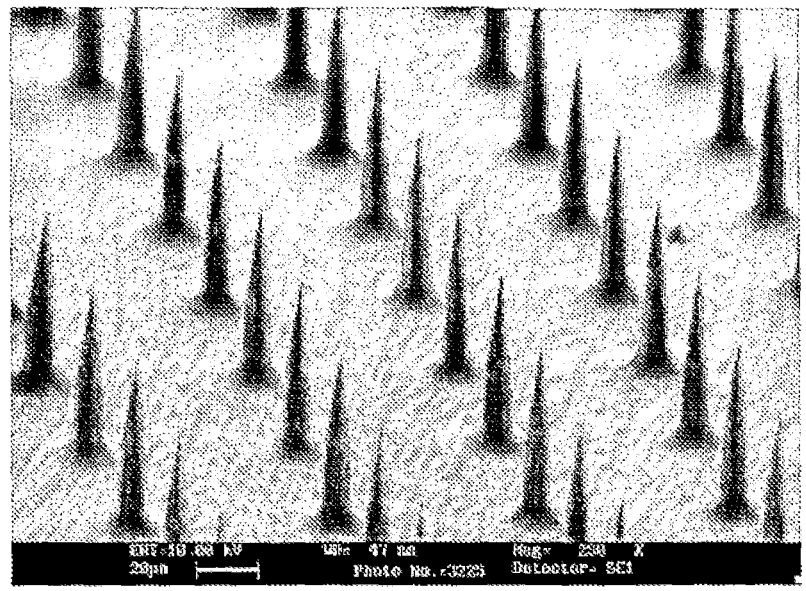
FIG. 21 is a secondary electron image of examples of projections having a hyper sharp tip.
Figure 22:
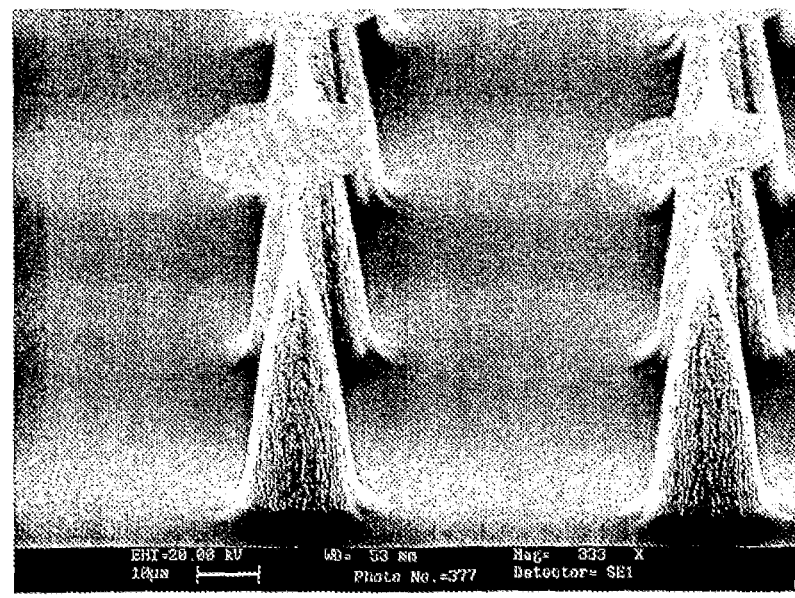
FIG. 22 is a secondary electron image of examples of projections having a conical convex 10o edge generated using a ramped etch process.

For the example of FIG. 21, the etching parameters are broadly as set out below, resulting in projections having a length of approximately 80-90 µm depth, hyper sharp, 5-to-1 base to length aspect ratio:
Etch mask 30 µm dot with 70 µm pitch
Resist: Su8-5 spun to give 15 µm thickness
Etch: gases 38 sccm $C_4F_8$ passivant, 62 sccm $SF_6$ etchant,
pressure 0.3 Pa (2.5 mT),
power 800 watts coil, 20 watts platen
time 90 minutes For the example of FIG. 22, the etching parameters are broadly as set out below. In this instance, a ramped etch is performed to result in a convex edge profile on projections having a length of approximately 60-70 µm:
Etch mask 30 µm dot with 70 µm pitch
Resist: Su8-5 spun to give 15 µm thickness
Etch: gases 50-80 sccm $C_4F_8$ passivant, 120 sccm $SF_6$ etchant,
pressure 0.3 Pa (2.5 mT),
power 800 watts coil, 20 watts platen
time 60 minutes—$C_4F_8$ gas ramped 0.5 sccm per minute It will be appreciated that the example etching parameters described above are for the purpose of example only and are not intended to be limiting. For example, the parameters will typically be etching system specific, so that if similar dimensioned projections are to be produced using different etching equipment, appropriate modification of the parameters will to be required.

Example experiments used to demonstrate the effectiveness of the projections at delivering material to subjects will now be described.

The tissue used in this experiment was mouse ear skin from 7 week old C57 Black6 female mice. Experimentation was performed in-vivo following injection of Ketamil-Xylasil anaesthetic (Troy laboratories Pty., Ltd., Smithfield, Australia), in accordance with Australian Animal Ethics guidelines. In-vivo tests ensured that blood flow was maintained to the skin to highlight erythema and blood vessel damage resulting from application. Five ears (n=5) were used per group in dye delivery and Cryo-SEM experiments.

The projection patches used for this study were designed to give a high probability of Langerhans cell-antigen interaction. The patches are fabricated using the etching techniques outlined above in a two step process, to thereby produce projections having a stepped configuration including a conical tip and cylindrical base. In this example, the projections have a length of 65 µm and a 50 µm conical section, atop a 15 µm cylindrical base. The projections have a density of 20,000/ $cm^2$, with 4 mm×4 mm projection area on a 5 mm×5 mm silicon base.

The delivery system for this experiment is a solid coating on the surface of the projections. This coating dissolves once wetted in the skin for the vaccine delivery. These studies were designed to emulate vaccine delivery. 8 µL solution of 0.4% Vybrant® DiD (a lipophilic fluorescent dye, Molecular Probes Inc., Eugene, Oreg.) and 1.5% Methylcellulose was coated on the array using a nitrogen jet method described in copending application number PCT/AU2008/001903. The dye is used to provide projection penetration tracks when the dye is released from the projections. Concentrations in solution were titrated for minimal diffusion following insertion.

Examples of coated and uncoated patches are shown in FIGS. 23A and 23B.

After patch application, the skin is prepared for confocal section dye measurement. To do this the skin is fixed in 2% Paraformaldehyde in 0.1 M Phosphate buffer, preceding cryo-preservation. Once frozen, 10 µm thick sections of skin were cut on a cryostat before imaging on a Zeiss LSM510 Meta confocal Multi-Photon Microscope (Carl Zeiss, Inc., Germany). Dye delivery highlighting projection tracks were measured in length from the point where the stratum corneum was breached at the edge of the hole, to the lowest dye point in the skin. An example of the sections used are shown in FIGS. 24A and 24B. Projection holes with significant stratum corneum deflection, obscuring the viable epidermis, were neglected as they represent incomplete penetration.

Surface data from microscopy allows information regarding projection penetration to be determined. This was done using a Scanning Electron Microscope (SEM) fitted with a cryo-stage and preparation chamber (Oxford CT-1500 and Philips XL30 SEM, Philips, Netherlands). For these studies the patches were coated as before, before application to the skin. The patch was applied to the skin in the same manner as in the dye studies. The patch and skin assembly was then slush frozen in liquid nitrogen ($LN_2$) and transferred to a cryo-preservation chamber under vacuum. At this point the patch was removed from the skin and the skin then sputter coated with a thin (few nanometers) layer of gold for imaging purposes. This technique ensures that the holes in the surface of the skin are as they would be n-situ. Skin morphology changes are restricted by the projections during the freezing, allowing accurate quantification. Imaging is then performed by SEM.

Application of an MNP patch to skin results in penetrative channels through the stratum corneum to lower layers of the skin, as shown in FIGS. 25A and 25B, in which significant holes are created over almost the complete 4 mm×4 mm area of the patch.

Using this technique the surface profile is clear, with individual corneocytes distinguishable. The location of the micro-channels with respect to the corneocytes (between or through) was seen to have no effect on penetration. The surface data also shows that areas with hair are punctured similarly to those without, indicating that the projections are not affected by hairs, simply puncturing through or adjacent to them.

The Cryo-SEM data also allows examination of the patch post-application where it is removed and an upper layer of corneocytes has remained on the projections. FIG. 26A shows the entire patch after application to mouse ear skin, whilst FIG. 26B shows a close-up of nine projections. The images show that the patch has large areas covered by to corneocytes which have been frozen with liquid nitrogen showing their profiles. The frozen corneocytes reveal penetration profiles and show the bulk behaviour of the outermost layer of skin. It is clear that for the case shown, the step in conical projection geometry is acting to restrain entrance to the skin. This is also evident in the FIG. 18C where there are circular impressions around projection holes at higher velocities indicative of the step reaching the skin. Projection progression appears to have been restricted by this.

The quantitative measurement of penetration performance of our MNP patch is from raw data such as the typical histological section shown in FIGS. 24A and 24B. This shows a section of mouse ear skin and the corresponding dye delivered. This can be used to measure delivery depth of dye payload, showing successful delivery beyond the stratum corneum. These data show that this device is capable of delivering molecules into the skin.

It is noticeable that the greatest penetration for these projections is approximately 65% of their conical length, which corresponds to the location at which skin reaches the step in geometry. In particular, when the cylindrical portion of the projections reach the surface of the skin they present a larger cross-sectional area to the corneocytes that they are touching, allowing the patch to be decelerated and penetration stopped. This is highlighted by viewing the treated area of skin after a 1.96 m/s application, where clear circular impressions around the projection holes are visible as shown in FIG. 25B.

Accordingly, it will be appreciated that the ability to perform a two step etch, and hence produce a stepped projection profile, allows the depth of projection penetration to be controlled in use, which can in turn be used to deliver payloads to specific cells or layers of cells in the skin. For example, in the case of vaccines, the viable epidermis, and Langerhans cells therein can be targeted directly using a stepped projection profile of appropriate length.

A number of further variations and options for use with the above described devices will now be described.

Herein, the terms "projection", "micro-nanoprojection", "nanoneedle", "nanoprojection", "needle", "rod" etc are used interchangeably to describe the projections.

The projections may be used for delivery not only through the skin but through other body to surfaces, including mucosal surfaces, to cellular sites below the outer layer or layers of such surfaces.

The device is suitable for intracellular delivery. The device is suitable for delivery to specific organelles within cells. Examples of organelles to which the device can be applied include a cell nucleus, or endoplasmic reticulum, for example.

In one example the device is provided having a needle support section, that is to say the projections comprise a suitable support section, of sufficient length to reach the desired site and a (needle) delivery end section having a length no greater than 20 microns and a maximum width no greater than 5 microns, preferably no greater than 2 microns.

In one example, the maximum width of the delivery end section is no greater than 1000 nm, even more preferably the maximum width of the delivery end section is no greater than 500 nm.

In a further example, the device is for mucosal delivery. This device may have a needle support section, that is to say the projections comprise a suitable support section, of sufficient length to reach the desired site, such as of length at least 100 microns and a (needle) delivery end section having a length no greater than 20 microns and a maximum width no greater than 5 microns, preferably no greater than 2 microns.

In one example, the device of the invention is for delivery to lung, eye, cornea, sclera or other internal organ or tissue. In a further example, the device is for in-vitro delivery to tissue, cell cultures, cell lines, organs, artificial tissues and tissue engineered products. This device typically has a needle support section, that is to say the projections comprise a suitable support section, of length at least 5 microns and a needle delivery end section having a length no greater than 20 microns and a maximum width no greater than 5 microns, preferably no greater than 2 microns.

In one example, the device comprises projections in which the (needle) delivery end section and support length, that is to say the "needle support section", is coated with a bioactive material across the whole or part of its length, as described in further detail in the copending application AU-2007907092. The (needle) delivery end section and support length may be coated on selective areas thereof. This may depend upon the bioactive material being used or the target selected for example.

In a further example, a bioactive material is releasably incorporated into the material of which the needle, or projection, is composed. All, or part of the projection may be constructed of a biocompatible, biodegradable polymer (such as Poly Lactic Acid (PLA), PolyClycolic Acid (PGA) or POLA or Poly Olucleic Acid), which is formulated with the bioactive material of choice. The projections may then be inserted into the appropriate target site and, as they dissolve, the bioactive material will enter the organelle(s)/cells.

In one aspect, the device is provided in the form of a patch containing a plurality of needles (projections) for application to a body surface. A multiplicity of projections can allow multiple cells and organelles to be targeted and provided with a material at the same time. The patch may be of any suitable shape, such as square or round for example. The overall number of projections per patch depends upon the particular application in which the device is to be used. Preferably, the patch has at least 10 needles per mm, and more preferably at least 100 needles per $mm^2$. Considerations and specific examples of such a patch are provided in more detail below.

As an alternative to a gold coating, any suitable biocompatible material may be provided as a coating, such as Titanium, Silver, Silicon, or the like. This may be the entire device, or alternatively it may only be the projections or the delivery end section of the projections which are made from the biocompatible materials.

An alternative means for producing masks is with 2 photon Stereolithography, a technique which is known in the art and is described in more detail below.

The device may be for a single use or may be used and then recoated with the same or a different bioactive material or other stimulus, for example.

In one example, the device comprises projections which are of differing lengths and/or diameters (or thicknesses depending on the shape of the projections) to allow targeting of different targets within the same use of the device.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method of producing projections on a patch, the method including:
   a) providing a mask on a substrate; and,
   b) etching the substrate using an etchant and a passivant to thereby control the etching process and form the projections, wherein the etching process is continuously controlled using the etchant and the passivant, and wherein the passivant does not include oxygen.

2. A method according to claim 1, wherein the mask includes an organic photo-resist.

3. A method according to claim 1, wherein the passivant is a gas including:
   a) at least one of:
   i) carbon; and,
   ii) silicon; and,
   b) at least one of:
   i) chlorine; and,
   ii) fluorine.

4. A method according to claim 1, wherein the passivant is at least one of:
   a) a per-fluoride hydrocarbon;
   b) a fluorinated olefine;
   c) Octafluorocyclobutane;
   d) Perfluoroisobutene; and,
   e) $C_4F_8$.

5. A method according to claim 1, wherein the etchant is a gas or plasma.

6. A method according to claim 1, wherein the etchant is sulfur hexa-fluoride.

7. A method according to claim 6, wherein a ratio of the etchant to the passivant is in the range of 0.25 to 0.60.

8. A method according to claim 6, wherein the etchant is supplied at a flow rate in the range of 0 to 200 sccm.

9. A method according to claim 1, wherein the method includes, chemically sharpening the projections.

10. A method according to claim 9, wherein the method includes, sharpening the projections by:
    a) forming a silicon dioxide layer on the projections; and,
    b) removing the silicon dioxide layer.

11. A method according to claim 10, wherein the method includes removing the silicon dioxide using 10% HF.

12. A method according to claim 1, wherein the method includes applying a coating to the projections.

13. A method according to claim 12, wherein the coating is a metallic coating.

14. A method according to claim 12, wherein the method includes using sputter deposition to deposit:
    a) an adhesion layer; and,
    b) a metallic layer on the adhesion layer.

15. A method according to claim 1, wherein the method further includes coating the projections with a therapeutic agent.

16. A method according to claim 1, wherein the patch has a surface area of approximately 0.4 $cm^2$.

17. A method according to claim 1, wherein the projections have a density of 20,000 projections/$cm^2$.

18. A method according to claim 1, wherein the projections have a length of 90 μm.

19. A method according to claim 1, wherein the projections have a radius of curvature of greater than 1 μm.

20. A method according to claim 1, wherein the projections include a support section and a targeting section.

21. A method according to claim 1, wherein the etching process is controlled by ramping etching parameters throughout the etching process.

22. A method according to claim 1, wherein the etching process is performed in multiple stages with different etching parameters being used for each stage.

23. A method according to claim 1, wherein the method includes performing a switched etching process following the continuously controlled etching process.

24. A method according to claim 1, wherein the method includes pausing the etching process and subsequently resuming the etching process.

25. A method according to claim 1, wherein the etching process uses a mixture of the etchant and the passivant.

26. A method according to claim 25, wherein the etching process is controlled by varying a ratio of the etchant to the passivant in the mixture.

27. A method according to claim 26, wherein the etching process is controlled by ramping the ratio throughout the etching process.

* * * * *